(12) United States Patent
Cook et al.

(10) Patent No.: US 8,193,213 B2
(45) Date of Patent: Jun. 5, 2012

(54) SPERMICIDAL AND/OR ANTIFUNGAL COMPOSITION AND METHODS OF USING THE SAME

(75) Inventors: Clarence E. Cook, Staunton, VA (US);
Carol D. Sloan, Hillsborough, NC (US);
Brian F. Thomas, Durham, NC (US);
Hernan A. Navarro, Chapel Hill, NC (US)

(73) Assignee: Research Triangle Institute, Research Triangle Park, NC (US)

( * ) Notice: Subject to any disclaimer, the term of this patent is extended or adjusted under 35 U.S.C. 154(b) by 638 days.

(21) Appl. No.: 12/277,708

(22) Filed: Nov. 25, 2008

(65) Prior Publication Data
US 2009/0149490 A1 Jun. 11, 2009

Related U.S. Application Data

(62) Division of application No. 10/350,232, filed on Jan. 24, 2003, now Pat. No. 7,544,696.

(51) Int. Cl.
*A61K 31/44* (2006.01)
*A01N 43/42* (2006.01)

(52) U.S. Cl. .................................................. 514/295
(58) Field of Classification Search ................... 514/295
See application file for complete search history.

(56) References Cited

U.S. PATENT DOCUMENTS

| | | | |
|---|---|---|---|
| 2,470,108 A | 5/1949 | Plati et al. | |
| 2,470,109 A | 5/1949 | Plati et al. | |
| 2,546,652 A | 3/1951 | Plati et al. | |
| 3,408,353 A | 10/1968 | Jucker et al. | |
| 3,462,443 A | 8/1969 | Paragamian | |
| 3,497,517 A | 2/1970 | Jucker et al. | |
| 3,574,686 A | 4/1971 | Jucker et al. | |
| 3,627,773 A | 12/1971 | Ebnother et al. | |
| 3,678,057 A | 7/1972 | Ebnother et al. | |
| 3,678,058 A | 7/1972 | Ebnother et al. | |
| 3,991,066 A | 11/1976 | Bastian et al. | |
| 5,314,917 A | 5/1994 | Michaels et al. | |
| 5,319,084 A | 6/1994 | Cook et al. | |
| 5,952,336 A | 9/1999 | Cook et al. | |
| 6,297,278 B1 | 10/2001 | Michaels et al. | |

FOREIGN PATENT DOCUMENTS

| | | |
|---|---|---|
| JP | 2001-511778 | 8/2001 |
| WO | WO 98/33525 | 8/1998 |

OTHER PUBLICATIONS

C. E. Cook, et al., J. Med. Chem., vol. 38, pp. 753-763, "Structure-Acitivity Studies of 2,3,4,4a,5,9b-Hexahydroindeno[1,2-*c*]Pyridines As Antispermatogenic Agents for Male Contraception", 1995.
G. De Meio, et al., Tetrahedron, vol. 49, No. 36, pp. 8129-8138, "Aryl Fluoride Syntheses Involving Reaction of Aryllead Triacetates With Boron Trifluoride-Diethyl Ether Complex", 1993.
C. E. Cook, et al., Journal of Medicinal Chemistry, vol. 40, No. 14, pp. 2111-2112, "Exceptionally Potent Antispermatogenic Compounds From 8-Halogenation of (4a*RS*,5*SR*,9b*RS*)-Hexahydroindeno-[1,2-*c*]Pyridines", Jul. 4, 1997.

(Continued)

*Primary Examiner* — San-Ming Hui
(74) *Attorney, Agent, or Firm* — Oblon, Spivak, McClelland, Maier & Neustadt, L.L.P.

(57) ABSTRACT

Hexahydroindenopyridine compounds are provided which act as spermicides and/or fungicides, spermicidal and/or fungicidal compositions containing the same, and methods for killing motile sperm and/or fungi using the compounds and compositions.

28 Claims, 4 Drawing Sheets

1. $R_3 = CH_3$
2. $R_3 = COOH$
3. $R_3 = COOMe$

OTHER PUBLICATIONS

S. A. Hild, et al., Biology of Reproduction, vol. 65, pp. 1771-1779, "Disruption of Spermatogenesis and Sertoli Cell Structure and Function by the Indenopyridine CDB-4022 in Rats", 2001.

S. A. Hild, et al., Biology of Reproduction, vol. 65, pp. 165-172, "Lupron Depot Prevention of Antispermatogenic/Antifertility Activity of the Indenopyridine, CDB-4022, in the Rat", 2001.

C. L.-T. Chang, et al., Biol. Pharm. Bull., vol. 25, No. 8, pp. 1097-1100, "Indenopyridine Hydrochloride Induced Testicular Spermatogenesis Failure With High Seminal Alkaline Phosphatase Levels in Male Dog", 2002.

P. A. Fail, et al., Reproductive Toxicology, vol. 14, pp. 265-274, "28-Day Toxicology Test: Indenopyridine RTI 4587-056 in Male Sprague-Dawley Rats", 2000.

J.M. Whitsett, et al. Effect of transitional photoperiods on testicular development and puberty in male deer mice (*Peromyscus maniculatus*), Journals of Reproduction & Fertility Ltd., vol. 72, pp. 277-286, 1984.

International Search Report, PCT/US04/00206.

Written Opinion, PCT/US04/00206.

Mutation Research 1979, 66(2), 113-127.

Merck Manual, 16$^{th}$ ed., 1992, p. 1774.

Nirmal K. Lohiya, et al., "Human sperm immobilization effect of *Carica papaya* seed extracts: an in vitro study" Asian Journal of Andrology, vol. 2, No. 2, 2000, pp. 103-109.

H Logothetou-Rella, "The inhibitor of calcium activated neutral proteinase is an anti-meiotic agent. The spermicidal and anti-viral action", Histology and Histopathology, vol. 10, 1995, pp. 271-282.

Anita P. Hoffer, et al., "Ultrastructural Fertility, and Spermicidal Studies with Isomers and Derivatives of Gossypol in Male Hamsters", Biology of Reproduction, vol. 37, No. 4, 1987, pp. 909-924.

Canadian Office Action issued on Mar. 24, 2011 in corresponding Canadian Application No. 2,514,047.

Office Action issued Dec. 30, 2012 in Canada Application No. 2,514,047.

1. $R_3$ = $CH_3$
2. $R_3$ = COOH
3. $R_3$ = COOMe a) HCl/H₂O, heat
b) SOCl₂
c) AlCl₃
d) p-BrC₆H₄Li
d) BF₃,Et₃SiH
f) KOH, n-BuOH, heat
g) n-BuLi; CO₂
h) SOCl₂, MeOH a) HCl/H$_2$O
b) SOCl$_2$
c) R(+)-or S(−)2,10-camphorsultam, n-BuLi
d) 2 mols p-tolylmagnesium bromide
e) aq.NH$_4$Cl
f) LiOH
g) SOCl$_2$
h) AlCl$_3$
i) p-bromobenzoic acid, n-BuLi
j) HCl/H$_2$O
k) see Figure 2, steps d-g
l) H$_2$/catalyst
m) KOH, n-BuOH, reflux
n) MeOH, SOCl$_2$

SPERMICIDAL AND/OR ANTIFUNGAL COMPOSITION AND METHODS OF USING THE SAME

BACKGROUND OF THE INVENTION

1. Field of Invention

The present invention is directed to hexahydroindenopyridine compounds which act as spermicides and/or antifungals, spermicidal or antifungal compositions containing the same, and methods for killing motile sperm or fungi using the compounds and compositions.

2. Discussion of the Background

In the US and much of the Western world, the high and growing demand for contraceptives is a function of lifestyle preferences, while in many developing nations, population control is a highly pressing public health concern. Considering that contraception is a global health need, albeit for different reasons in different parts of the world, the total market for a male contraceptive could be much larger than that accounted for in the US figures alone.

In the Western World, the market for contraceptives has changed relatively little over the past 50 years, with "the pill" having been developed in 1951 and remaining unparalleled as the popular choice for contraception. Advances in contraception research have only offered a few more choices, all to women, who have historically born the brunt of the responsibility, cost, and health-risk (in particular, risks of cardiovascular disease and certain types of cancer associated with long-term use of hormonal-based contraceptives) of contraception. The condom, invented in the 16th century, is the only significant form of contraception available to men (other than "withdrawal" and vasectomy). The only real innovative improvement that has occurred with the condom came with the vulcanization of rubber in the 19th century.[1]

[1] From New Scientist, 20 Apr. 1994, Vol 142 No 1923.

As pharmaceutical companies develop compounds for sexual dysfunction (e.g., Viagra for erectile dysfunction), the demand for contraceptives is expected to grow. Condom sales in the U.S. rose 5.8% during 1999, generating $260 million in revenue, reflecting what some have called a new American sexual revolution.[2] Although the majority of women of child-bearing age already practice contraception[3], still half of all pregnancies are unintended.[4] There has been a persistent appeal from health and consumer groups for more alternatives, in particular for alternatives that allow men to assume a greater portion of contraceptive responsibility. Global concerns have led organizations such as the World Health Organization and Family Health International to launch initiatives aimed at encouraging the development of male contraceptives. At least two companies, Schering and Organon, are investing heavily to bring a hormonal male contraceptive to market within this decade.

[2] Drug Store News, Nov. 29, 1999 v21 i19 p29.
[3] 58% of all married women in the world of reproductive age use some sort of contraceptive method (The Population Division of the United Nations Department of Economic and Social Affairs 2000).
[4] NICHD, Contraception and Reproductive Health Branch: Report to the NACHHD Council September 1999.

Safe and effective orally active male contraceptive drugs have been sought for many years. However, the development of a drug which can safely interrupt spermatogenesis without affecting libido and thereby function as a male contraceptive agent has proven to be a difficult task.

An ideal contraceptive for the male would be one that effectively arrests the production of spermatozoa, blocks their fertilizing capacity without affecting libido or accessory sex organs and their functions, and/or kills motile spermatozoa. In addition it should have a wide separation of effective and toxic doses, and the method should be reversible. Such an ideal male contraceptive agent is currently unavailable.

Some general cellular toxicants such as anticancer agents and alkylating agents affect spermatogenesis, but are obviously not acceptable as contraceptives. Compounds which interfere with cellular energy processes, such as thiosugars also interfere with spermatogenesis, are not sufficiently selective. Androgens such as testosterone and its analogs, when given in sufficiently high doses, interfere with spermatogenesis, probably through a mechanism involving the hypothalamic-pituitary axis. These steroid compounds have been used successfully in clinical studies. However, the anabolic properties of these steroids may give rise to undesirable side effects.

Gonadotrophin releasing hormone (GNRH) analogs have been actively investigated as compounds which effectively block spermatogenesis. However, GNRH analogs interfere with endogenous testosterone production and thus decrease libido unless supplementary androgens are administered.

One approach to male contraceptives is based on identification and exploitation of the biochemistry of the male reproductive process. The testis consists of three functional compartments. The first, responsible for the production of sperm, consists of seminiferous tubules which contain developing germ cells. The second is the Sertoli cell, also located inside the seminiferous tubule, which contributes to the organizational and functional coordination of the spermatogenic process and probably has paracrine and autocrine roles. Due to the complex organizational relationship between the Sertoli cell and the developing germ cells, and the presence of tight junctions between neighboring Sertoli cells, a blood testis barrier is formed, dividing the seminiferous tubule into areas that are isolated from the direct access by blood-borne chemicals or nutrients. Surrounding the tubules, in the interstitial tissue, are Leydig cells that have several endocrine and paracrine functions, the production of testosterone being the best described.

The germinal cells divide and differentiate progressively, moving as they mature from the basement membrane to the tubule lumen. Spermatogonia lie in the basal compartment, and selectively recruited spermatogonia divide mitotically to become either cells that persist as spermatogonia or differentiate into primary spermatocytes. The primary spermatocytes migrate through the junctions between the Sertoli cells and divide meiotically to form secondary spermatocytes. Secondary spermatocytes divide to form spermatids. The spermatids then differentiate into mature spermatozoa. Differentiation of the spermatids is often termed spermatogenesis. However, for the purposes of this application, "spermatogenesis" is defined to cover the entire process of formation and maturation (differentiation) of sperm and an "antispermatogenic compound" is one which disrupts any part of this process.

A summary of Sertoli cell functions is as follows: (a) support and nutrition to the seminiferous epithelium, (b) release of late spermatids into the tubule lumen, (c) formation of a morphological and physiologic blood testes barrier, (d) phagocytosis of degenerating germ cells, and (e) regulation of the cycle of seminiferous epithelium.

The Leydig cell also supports spermatogenesis. Luteinizing hormone (LH) from the pituitary stimulates testosterone production by the Leydig cell. Testosterone and its metabolite, dihydrotestosterone, are necessary to support normal spermatogenesis. Testosterone receptors are present on various germ cell types. Testosterone is delivered through the blood testis barrier, likely through transport into the Sertoli cell, where it is metabolized into estradiol, dihydrotestosterone, or remains unaltered.

Some, if not all of the germ cell types, interact with the Leydig and/or Sertoli cell. These interactions are in the form of chemical messengers that are produced by Sertoli, Leydig, and germ cell(s). For example, the pachytene spermatocyte modulates the secretion of a Sertoli cell proteinaceous factor that in turn stimulates steroidogenesis by the Leydig cell. The binding of spermatids occurs only to Sertoli cells which are rendered competent or functional by exposure to FSH. The Sertoli cell of rats secretes several proteins in a cyclic fashion, with maximal production occurring at a specific stage of the seminiferous epithelium; that is, when it is in association with a specific group of germ cells. Clusterin is produced maximally by Sertoli cells when the seminiferous epithelium is in a Stage VII or VIII configuration that is independent of FSH stimulation, suggesting a local regulation of Sertoli secretory function by germ cells.

Hexahydroindenopyridine compound no. 20-438 developed by Sandoz, Ltd. (compound 1 in FIG. 1) has been shown to provide reversible inhibition of spermatogenesis on oral administration to animals. See Arch. Toxicol. Suppl., 1984, 7:171-173; Arch. Toxicol. Suppl., 1978, 1:323-326; and Mutation Research, 1979, 66:113-127.

The synthesis of a variety of indenopyridine compounds as racemic mixtures is known and described, for example, in U.S. Pat. Nos. 2,470,108; 2,470,109; 2,546,652; 3,627,773; 3,678,057; 3,462,443; 3,408,353; 3,497,517; 3,574,686; 3,678,058 and 3,991,066. These indenopyridine compounds have a variety of uses including use as serotonin antagonists exhibiting antiphlogistic and analgesic properties, hematoblast aggregation inhibitors, sedatives, and neuroleptic compounds as well as ulcer-protective, hypotensive and anorexigenic compounds.

U.S. Pat. Nos. 5,319,084 and 5,952,336 disclose hexahydroindenopyridine compounds having antispermatogenic activity in which the 5-position is substituted with a phenyl ring having a para-position substituent.

Despite extensive research in this field, a need continues to exist for active reversible male antifertility drugs which have limited side-effects. A continuing problem is the need to administer known compounds at dosage levels which may cause side-effects. An additional problem in this field is the lack of suitable imaging agents having specific binding sites on or in the testes. A need continues to exist for compounds which may be used as imaging agents in the study of testicular function and in the diagnosis of testicular malfunction.

In addition to male oral contraceptives, there is a need for more effective spermicidal compositions for use as traditional topical/external contraception practices.

SUMMARY OF THE INVENTION

Accordingly, one object of the present invention is to provide an orally active male contraceptive drug which does not affect libido, has high potency and activity, and has minimal side effects or toxicity.

A further object of the present invention is to provide an orally active male contraceptive drug which inhibits spermatogenesis and a method of inhibiting spermatogenesis using this drug.

A further object of the present invention is to provide a composition which acts as a spermicide, killing motile sperm, thus being effective as a contraceptive agent for external application.

It is a further object of the present invention to provide a composition which acts as an antifungal composition.

These and other of the objects of the present invention have been achieved by the discovery of the hexahydroindenopyridine compounds of the present invention and the discovery that these compounds are highly potent, interrupt spermatogenesis and act as a spermicide on motile sperm, and which exhibit effective anti-fungal properties.

The compounds of the present invention solve the problems noted above. The compounds of the invention exhibit high potency at lower relative dosages than known compound 1 and reduce the occurrence of side-effects, such as the sedative effects observed with this compound. Further, the compounds of the invention interact with a macromolecular site in the testes. The compounds of the invention which contain a label, such as a radioactive label, overcome the problem of inadequate imaging agents by providing an imaging agent which is useful in the study of testicular function and the diagnosis of testicular malfunction. The compounds of the present invention have also been found to act as a spermicidal agent, killing motile sperm in a highly effective and efficient manner, suggesting their use in a variety of spermicidal compositions. It has also been found that the present invention compounds act as an anti-fungal.

DETAILED DESCRIPTION OF THE INVENTION

Figure 1:
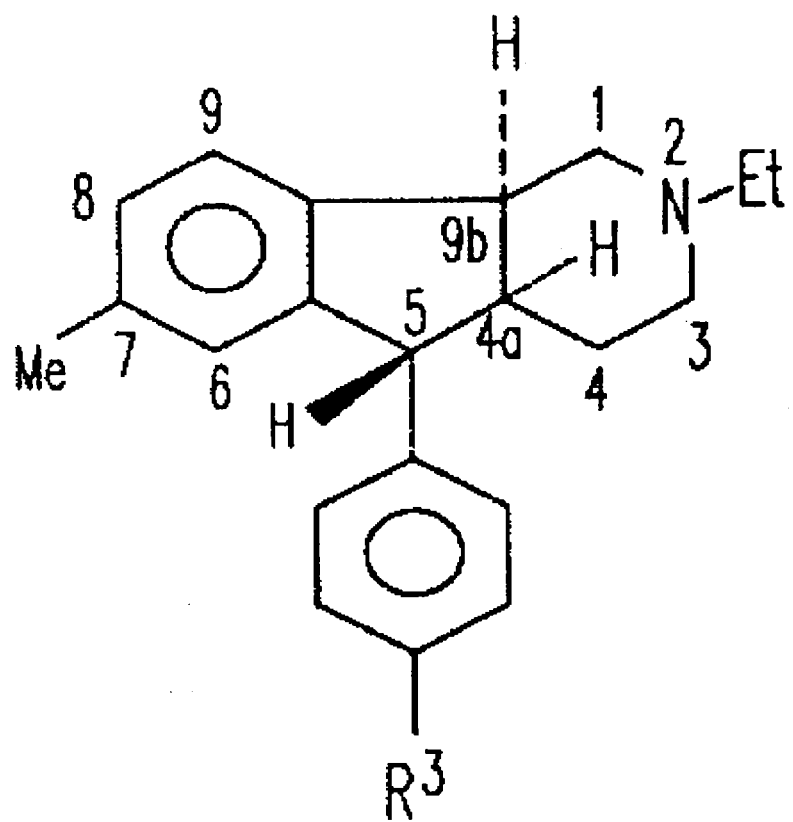
FIG. 1 shows the structure of three hexahydroindenopyridine compounds and indicates the numbering system for these compounds.

It has now been discovered that hexahydroindenopyridine compounds having the structure I(a) shown below, preferably having the structure shown in I(b) below:

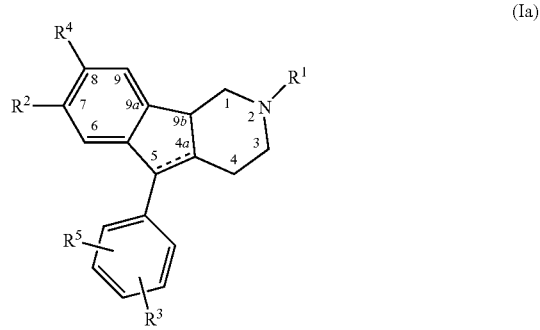

(Ia)

-continued

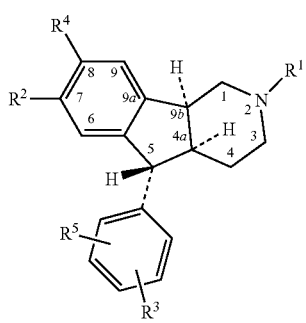

(Ib)

wherein the hydrogen atoms at positions 4a, 5 and 9b have the relative stereochemistry shown (hydrogens at positions 4a and 5 are trans, hydrogens at 4a and 9b are cis to one another; Formula I(b)); or the relative stereochemistry at position 9b can be reversed so that hydrogens at positions 4a and 5 are trans, hydrogens at 4a and 9b are trans to one another; or all three hydrogens can be cis to one another; or wherein the dashed line between 4a and 5 indicates that the compound may also be the 4a,5-dehydro compound, thus having a double bond between carbons 4a and 5 and where $R^1$ is hydrogen or straight-chain or branched $C_{1-6}$ alkyl, preferably $C_{1-3}$ alkyl, or $C_3$-$C_8$ cycloalkyl; $R^2$ is hydrogen, straight-chain or branched $C_{1-6}$ alkyl, preferably $C_{1-3}$ alkyl; $R^3$ and $R^5$ are independently hydrogen, halogen, $SO_3H$, straight-chain or branched $C_{1-6}$ alkyl, $CH_2OH$, $CH_2OMe$, straight chain or branched $C_{1-6}$ alkoxy, carboxyl (COOH) or a group which can be converted under mammalian physiological conditions to a carboxyl group, carboxylic acid ester (COOR where R is $C_{1-10}$ alkyl, $C_{6-10}$ aryl, $C_{7-10}$ aralkyl), hydroxymethyl ester ($CH_2OC(O)$—R where R is as defined above), $CONH_2$, CONHR, $CONR_2$, $CH_2OCONHR$, CN, CH=$NHNHCONH_2$, and halogen; and $R^4$ is hydrogen, halogen, $R_3Si$ or COR are not only antispermatogenic and have activities as much as about 40 times the oral anti-spermatogenic activity of the best known compounds as reported in previous U.S. Pat. No. 5,319,084, but also act as a spermicide to kill motile sperm, and also act as an anti-fungal agent.

Within the context of the present invention, the term "antispermatogenic" relates to the ability to disrupt the production of sperm in the testes, while the term "spermicide" or "spermicidal" relates to the ability to kill motile sperm after their production and, more preferably, after ejaculation.

The compounds of the present invention have the relative stereochemistry shown in structure (I). This invention includes both individual enantiomeric forms (essentially optically pure) as well as any mixtures of these forms, for example, a racemic mixture.

Pharmaceutically acceptable salts of the compounds having structure (I) shown above are also included within this invention. Pharmaceutically acceptable salts include, but not are limited to salts of a basic functional group (such as but not limited to an amine group) with inorganic acids such as hydrochloride, hydroiodide, sulphate, phosphate, diphosphate, hydrobromide and nitrate or salts of the basic functional group with an organic acid such as acetate, malate, maleate, fumarate, tartrate, succinate, citrate, lactate, methanesulfonate, p-toluenesulfonate, palmoate, salicylate and stearate; or salts of an acidic functional group with metal ions such as (but not limited to) Na, K, Ca or salts of an acidic functional group with the ammonium ion, or salts of an acidic functional group with organic ions such as (but not limited to) amines and tetrasubstituted ammonium ions.

Substituent $R^1$ is preferably a straight-chain alkyl (n-alkyl), iso-alkyl or cycloalkyl group, such as methyl, ethyl, n-propyl, iso-propyl, n-butyl, iso-butyl, n-pentyl, iso-pentyl, n-hexyl, iso-hexyl, cyclopropyl, cyclopentyl, cyclohexyl. Most preferably, $R^1$ is ethyl.

Substituent $R^2$ is also preferably a straight-chain or iso-alkyl group as described for $R^1$ described above.

Substituent $R^3$ is preferably in the para or 4 position of the ring and is preferably a group selected from hydroxymethyl ($CH_2OH$), formyl (CHO), carboxyl (COOH), carboxylic acid ester (COOR where R is $C_{1-10}$ alkyl, $C_{6-10}$ aryl, $C_{7-10}$ aralkyl), and hydroxymethyl ester ($CH_2OC(O)$—R where R is as defined above), $CONH_2$, CONHR, $CONR_2$, $CH_2OCONHR$, CN, CH=$NHNHCONH_2$, and halogen.

Substituent $R^4$ is preferably halogen including I, Br, Cl and F. The potent activity of these compounds is surprising. The halogen may be a radioactive isotope, for example $^{123}I$, $^{125}I$, or $^{131}I$. Other radioactive isotopes, such as for example $^{11}C$, tritium ($^3H$) or $^{18}F$, or radioactive isotopes of bromine and chlorine, may be substituted for the usual (nonradioactive) isotopes in the above compounds.

Compound 1 is a racemic mixture. The structure of compound 1 is shown in FIG. 1, compound 1. Hexahydroindenopyridines have three asymmetric centers which can be defined using known nomenclature. Alternatively the relative stereochemistry can be defined by the cis-trans relationships of the hydrogen atoms bonded to the carbon system at positions 4a, 5 and 9b of the tricyclic ring system, leading to stereochemical assignments. Following the Cahn-Ingold-Prelog nomenclature, the stereochemistry and name of compound 1 is (4aRS,5SR,9bRS)-2-ethyl-2,3,4,4a,5,9b-hexahydro-7-methyl-5-(4-methylphenyl)-1H-indeno[1,2-c]pyridine.

Compound 1 has a hydrophobic methyl substituent on the 5-phenyl group corresponding to substituent $R^3$ in structure (I) shown above. The antispermatogenic activity of compound 1 resides essentially exclusively in the (+) isomer (the optical rotation is dextrorotatory when measured under the conditions described in Cook et al., 1995), which is an effective antispermatogenic drug in mice. Antispermatogenic activity of other compounds of this series also resides essentially exclusively in one optical isomer. The measured optical rotation of these compounds, however, may be either (+) or (−), depending on the substitution pattern and the conditions of measurement, as is known to those skilled in stereochemistry. On the other hand, the antifungal properties of the compounds of the present invention are not stereospecific, with both (+) and (−) isomers active, although their relative activities may differ.

The spermicidal effects of the compounds of the present invention have been found in the antispermatogenic isomers and are believed to be present also in the other isomers.

The very polar carboxyl group or groups which can be metabolized under mammalian physiological conditions to a carboxyl group may be present at any position, preferably the para-position, of the 5-phenyl ring of the compounds of the invention with retention of spermicidal and/or antifungal activity. For example, compounds in which the para-position is substituted with hydroxymethyl ($CH_2OH$), formyl (CHO), carboxyl (COOH) and methoxycarbonyl ($C(O)OCH_3$) groups retain potent activity. These compounds exhibit activity despite the presence of a polar substituent in the para-position of the 5-phenyl ring.

By "metabolized under mammalian physiological conditions" is meant a functional group $R^3$ which is converted to a carboxyl group when a compound having structure (I) is administered to a living mammal for which antispermatogenic treatment is desired. Administration may be by any conventional means or route, including but not limited to, oral, interperitoneal, intraveneous, subcutaneous, intramuscular, inhalation, buccal and skin penetration. These same administration routes are available for spermicidal and/or antifungal treatments, along with topical administration. The conversion of the group $R^3$ to a carboxyl group is readily determined by monitoring metabolites of the compound having structure (I) in the blood or in the urine. The metabolites may be monitored using conventional analysis methods such as mass spectrometry (MS), gas chromatography (GC), etc.

Preferably, at least 50%, more preferably at least 80% and even more preferably 90%, 95% or 100% of functional groups $R^3$ are metabolized to a carboxyl group upon administration to the mammal, although this is not necessary in order to obtain spermicidal and/or fungicidal properties. The percentage of conversion can be determined by quantitatively analyzing a blood or urine sample to determine the relative amounts of unconverted compounds containing functional group $R^3$ relative to compounds in which $R^3$ has been converted to a carboxyl group using one of the conventional analysis methods noted above.

The antispermatogenic activity of compound 1 is observed after a single oral dose of 30 mg/kg to rats, drastically reducing the weights of the testes within 24 h. Degenerative changes in the seminiferous tubules are observed. Spermatids became pycnotic, occasionally forming multinucleated associations. Sertoli cells appear to be cytologically normal. It appears that compound 1 targets spermatids or the Sertoli cell associated with these spermatids because histologic changes are observed in these spermatids first.

Compound 1 causes some lethargy and sedation in mice at an oral dose of 30 mg/kg and extreme lethargy at the same dose given subcutaneously. Lethargy and sedation are obviously undesirable side effects in contraceptive agents. In contrast to the lethargy and sedation observed with compound 1, the compounds of the present invention produce minimal lethargy.

The compounds of the present invention allow one to separate the antifertility activity from the sedative activity observed with compound 1. The compounds of the invention are, therefore, effective antifertility drugs in which the undesired side-effects of sedation and lethargy are markedly diminished.

The compounds of the invention were tested in mice for their effects on spermatogenesis three days after a single oral dose by the procedure described in Cook et al (1995) below. Compounds active in this test have been shown also to be anti-fertility compounds.

Compounds were screened for antispermatogenic activity by dosing male mice on day 1 with a gavage dose of control vehicle, positive control (compound 1) or compound of the invention. At 72 h after dosing, animals were killed and the testes were excised, trimmed of fat, and weighed. One testis was examined histologically and rated for spermatogenic potential using the Spermatogenic Index (J. M. Whitsett, P. F. Noden, J. Cherry and A. D. Lawton, J. Reprod. Fertil., 72, 277 (1984), which is a semiquantitative estimate of the sperm producing ability of the testes The index is based on histological appearance of the spermatogenic cells in the seminiferous tubules. A scale of 1 to 6 is used with 5 to 6 being the normal status. A second assessment was based on the weight of the testes.

Tables 1 and 2 show pertinent biological results in terms of the change in testes weight (TW) and spermatogenic index (SI) relative to a control containing only the administration vehicle, but no indenopyridine. In Tables 1 and 2, $R^3$ and $R^4$ refer to structures Ib, where $R^3$ is in the para position; $R^1$ is ethyl; $R^2$ is methyl; and $R^5$ is hydrogen.

With an 8-iodo-7-methyl-4'-carboxy or 4'-carbomethoxy substituent pattern, an oral dose of 2 µmol/kg (1 mg/kg) of the racemate resulted in a 57-67% decrease in the spermatogenic index and was at least as effective as a 79 µmol/kg (30 mg/kg) dose of the corresponding analog without the 8-iodo substituent. In the case of the 8-bromo or 8-chloro analogs, the lowest dose tested (6 or 2 µmol/kg; 3 or 1 mg/kg) was also at least as effective as the 79 µmol/kg (30 mg/kg) dose of the non-halogenated analog (see Table 1). Comparison of the active (levo) enantiomer of the 8-iodo-7-methyl-4'-carbomethoxy analog with the active enantiomer of the 8-H-7-methyl-4'-carbomethoxy analog (Table 2) showed the former compound to have the same or greater effect at 0.6 and 2 µmol/kg (0.3 and 1 mg/kg) as the latter compound at 25 and 75 µmol/kg (10 and 30 mg/kg). Thus, an approximately 40-fold increase in molar potency was achieved by halogenation of the 8-position.

TABLE 1

THE ANTISPERMATOGENIC EFFECT OF RACEMIC INDENOPYRIDINE COMPOUNDS IN ADULT MALE SWISS MICE[a]

| Compd | $R^3$ | $R^4$ | Dose (mg/kg) | TW[b] change (%) | SI[c] change (%) |
|---|---|---|---|---|---|
| 1 | Me | H | 30 | 19%* | −55%* |
| 2 | $CO_2H$ | H | 10 | 2% | −24%* |
| 2 | $CO_2H$ | H | 30 | −7% | −52%* |
| 18 | $CO_2Me$ | I | 1 | −16% | −57%* |
| 18 | $CO_2Me$ | I | 3 | −27%* | −69%* |
| 18 | $CO_2Me$ | I | 10 | −36%* | −74%* |
| 17 | $CO_2H$ | I | 1 | −18% | −67%* |
| 17 | $CO_2H$ | I | 3 | −9% | −66%* |
| 17 | $CO_2H$ | I | 10 | −32%* | −76%* |
| 19 | $CO_2H$ | Br | 3 | −8% | −69%* |
| 19 | $CO_2H$ | Br | 10 | −28%* | −71%* |
| 19 | $CO_2H$ | Br | 30 | −39%* | −72%* |
| 20 | $CO_2H$ | Cl | 1 | −16% | −55%* |
| 20 | $CO_2H$ | Cl | 3 | −23% | −66%* |
| 20 | $CO_2H$ | Cl | 10 | −22% | −72%* |

[a]Values are calculated from the means (n = 5) as [100(test−control)/control].
Only the highest dose is shown for compounds that were inactive.
A single dose of indenopyridine or vehicle was given to mice by gavage at 10 ml/kg.
Vehicle was 90% water, 7% Tween20, and 3% ethanol.
Necropsy was conducted on day 3, beginning about 72 h postdosing.
[b]Testes weight [% change from vehicle control of 217.8 +/− 46.0(S.E.) mg]
[c]Spermatogenic Index [% change from vehicle control of 5.8 +/− 0.2(S.E.)]
*Significantly different from vehicle control; Dunnett's onetailed T test, p < 0.05.
Statistical analysis was performed on the raw data before conversion to % change.

TABLE 2

THE EFFECT OF 8-IODINATION ON THE ANTI-SPERMATOGENIC EFFECT OF CHIRAL INDENOPYRIDINE COMPOUNDS IN ADULT MALE SWISS MICE[a]

| Compd | $R^3$ | $R^4$ | Dose (mg/kg) | TW[b] Change (%) | SI[c] change (%) |
|---|---|---|---|---|---|
| 1 | Me | H | 30[d] | −24%* | −61%* |
| 3 (l) | $CO_2Me$ | H | 1 | 8% | 3% |
| 3 (l) | $CO_2Me$ | H | 3 | −12% | −2% |
| 3 (l) | $CO_2Me$ | H | 10[e] | −13% | −33%* |
| 3 (l) | $CO_2Me$ | H | 30 | −30%* | −64%* |
| 18 (l) | $CO_2Me$ | I | 0.3 | −11%* | −34%* |
| 18 (l) | $CO_2Me$ | I | 1 | −21%* | −66%* |

TABLE 2-continued

THE EFFECT OF 8-IODINATION ON THE ANTI-
SPERMATOGENIC EFFECT OF CHIRAL INDENOPYRIDINE
COMPOUNDS IN ADULT MALE SWISS MICE[a]

| Compd | $R^3$ | $R^4$ | Dose (mg/kg) | $TW^b$ Change (%) | $SI^c$ change (%) |
|---|---|---|---|---|---|
| 18 (l) | $CO_2Me$ | I | 3 | −27%* | −71%* |
| 18 (l) | $CO_2Me$ | I | 10[e] | −31%* | −72%* |

(COMPOUND 1 IS THE RACEMATE; COMPOUNDS 3 AND 18 ARE THE LEVORO-TATORY (l) ISOMERS)
[a]Values were calculated from the means (n = 5) as [100(testcontrol/control)].
A single dose of indenopyridine or vehicle was given to mice by gavage at 10 ml/kg.
Necropsy was conducted on Day 3, beginning about 72 h postdosing.
Vehicle was 1% Tween20 in water.
[b]Testes weight (% change from vehicle control of 227.5 +/− 8.6 mg).
[c]Spermatogenic Index (% change from vehicle control of 5.7 +/− 0.2)
[d]n = 6
[e]n = 4
*Significantly different from vehicle control; Dunnett's onetailed T test, p < 0.05.
Statistical analysis was performed on the raw data before conversion to % change.

The spermicidal activity of the compounds of the present invention is significantly present with only a single application of composition to ejaculate, with the composition having a concentration of only 3 μM significantly diminishing motility, with motility dropping to zero after application of composition of the present compounds having concentration of only 100 μM. The spermicidal composition of the present invention can have any concentration sufficient to decrease motility of the spermatozoa to a level insufficient to cause impregnation, preferably a concentration of from 1-500 μM, more preferably from 3-300 μM, most preferably from 10-200 μM. Spermicidal activity was determined by the method described below.

Method for Determining Direct Effect of an Agent on Sperm Motility

The direct effect of an agent on sperm motility was determined by using the following protocols. Basically, sperm are obtained either from the cauda epididymis, as in the case of the rat, or ejaculated sperm collected using an artificial vagina, as in the rabbit. The initial motility of the sperm is determined manually or by using a Hamilton Thorn IVOS sperm analyzer. The sperm are then kept at a constant temperature of 34° C., diluted to a consistent concentration of 10×106/ml, and added to about 3 ml of buffer or media. The motility is determined again at this point and any change is recorded. Different concentrations of the agent to be tested are then added to the sperm preparation. The sperm samples are then held at the same temperature for one hour and the motility is determined. The results are recorded as the percent of motile sperm in the sample.

Protocol for Determination of a Direct Effect of an Agent on Sperm Motility

General:

The Sperm were kept at 34° C. throughout the experimental period. Sperm concentration was be approximately $10 \times 10^6$/ml (note, the sample may have had to be diluted with buffer or media to reach this concentration).

For the Rat Studies: (Using Sperm from the Cauda Epididymis)

A 1 mM stock of the indenopyridine in HBSS buffer+BSA (5 mg in 10=0.5 ug/ul; 0.5 ug/ml=1 uM) was prepared and added as follows:

1 uM=1 ul stock+949 ul HBSS buffer+BSA+50 ul of the diluted sperm
3 uM=3 ul stock+947 ul HBSS buffer+BSA+50 ul of the diluted sperm
10 uM=10 ul stock+940 ul HBSS buffer+BSA+50 ul of the diluted sperm
30 uM=30 ul stock+920 ul HBSS buffer+BSA+50 ul of the diluted sperm
100 uM=100 ul stock+850 ul HBSS buffer+BSA+50 ul of the diluted sperm
300 uM=300 ul stock+650 ul HBSS buffer+BSA+50 ul of the diluted sperm
1000 uM=1000 ul stock+50 ul of the diluted sperm Sperm Motility was determined after 1 hour.

For the Rabbit Studies: (Using Ejaculated Sperm)

A 1 mM stock of the indenopyridine in M-199 media with BSA (2.5 mg in 5=0.5 ug/ul; 0.5 ug/ml=1 uM) was prepared and added as follows:

1 uM=1 ul stock+949 ul M-199 media with BSA+50 ul of the diluted sperm
3 uM=3 ul stock+947 ul M-199 media with BSA+50 ul of the diluted sperm
10 uM=10 ul stock+940 ul M-199 media with BSA+50 ul of the diluted sperm
30 uM=30 ul stock+920 ul M-199 media with BSA+50 ul of the diluted sperm
100 uM=100 ul stock+850 ul M-199 media with BSA+50 ul of the diluted sperm
300 uM=300 ul stock+650 ul M-199 media with BSA+50 ul of the diluted sperm
1000 uM=1000 ul stock+50 ul of the diluted sperm Sperm motility was determined after 1 hour.

Slides were made to determine morphology changes and eosin was added to determine cell death.

The results of spermicidal tests are shown in Table 3 (rabbit ejaculate) and Table 4 (rat cauda sperm) below.

TABLE 3

Rabbit Sperm Motility

| Ejaculate ID | Ejaculate Volume (ml) | Ejaculate Concentration (×10$^6$) | Initial Motility (%) | Motility (%) at 60 Minutes |
|---|---|---|---|---|
| Neat Sample | 0.7 + plug | 132 | 78.8 | 76.8 |
| Control (Neat diluted 1:10) | | | 78.5 | 76.6 |
| +1 μM 073L | | | | 73.0 |
| +3 μM 073L | | | | 68.4 |
| +10 μM 073L | | | | 67.6 |
| +30 μM 073L | | | | 61.9 |
| +100 μM 073L | | | | 15.2 * |
| +300 μM 073L | | | | 0 |
| +1000 μM 073L | | | | 0 ** |

* Motility not progressive - twitching
** Sperm appeared to be "disintegrating"- sperm heads contain many vacuoles and membranes are not always intact

TABLE 4

Rat Cauda Sperm Motility

| | Motility (%) at 60 Minutes |
|---|---|
| Control 0 μM | Progressive motility |
| +1 μM 073L | Progressive motility-equal to control |
| +3 μM 073L | Progressive motility diminished |
| +10 μM 073L | No progressive motility - twitching |
| +30 μM 073L | Same as for 10 μM |
| +100 μM 073L | Death |

The fungicidal activity of the compounds of the present invention can be obtained at any concentration sufficient to reduce the fungal level to a level insufficient to cause fungal infection, and is preferably obtained at concentrations of from 1-500 µM, more preferably at concentrations of from 20-300 µM, most preferably from 20-200 µM.

Antifungal susceptibility testing was performed following the NCCLS guidelines with minor modifications. Briefly, a suspension of Candida albicans cells was prepared from pure cultures grown overnight on yeast-malt extract (YM) agar at 35° C. Several small colonies were removed from a YM agar plate and transferred to 5 ml of 0.85% saline. The cells were suspended by 15 seconds of vortexing and the cell density of the resulting suspension was determined using a spectrophotometer. The cell density was adjusted by addition of 0.85% saline until the transmittance matched that of a 0.5 McFarland standard when measured at a wavelength of 530 nm. An aliquot of this suspension was diluted 1:1000 in RPMI-MOPS to yield a working suspension. A similar suspension of Aspergillus fumigatus spores was obtained by using spores stored at 40 C in 0.85% saline. These spores were diluted in 0.85% saline to match the McFarland standard transmittance. This suspension was then further diluted 1:50 in RPMI-MOPS to produce the working inoculum suspension.

Dilution series of the test compounds were made in RPMI-MOPS containing 2% DMSO. An aliquot of each dilution was added in duplicate to the wells of a sterile 96-well, flat bottom microtiter plate. Then, an aliquot of either the C. albicans cell suspension or the A. fumigatus spore suspension were added to each well for a final volume of 200 µl. The plates were then incubated at 350 C. After 19 hours of incubation, the C. albicans inoculated plates were observed using the unaided eye for determination of minimal inhibitory concentration (MIC), the concentration for which there was no observable growth. A similar determination was made for the A. fumigatus plates after 48 hours. For all dilutions that exhibited no growth of the test organism, the minimal fungicidal concentration (MFC) was determined by streaking 100 µl of medium from a representative well onto a YM agar plate for growth of C. albicans or potato dextrose agar plate for A. fumigatus. The numbers of colony forming units (CFU) were counted and these values used to calculate the percent survival of cells or spores in inocula relative to the number of CFUs in the working inoculum suspension. The minimum fungicidal concentration (MFC) was the lowest concentration of test compound with a percent survival of less than 2%.

The results of fungicide tests are shown in Tables 4-6 below.

TABLE 4

FUNGICIDAL ACTIVITY AGAINST C. ALBICANS

| Compound | C. albicans (19 hours) | | | |
|---|---|---|---|---|
| | Lowest | CFU for MFC | | |
| — | [Active] | 300 | 200 | 100 |
| 4587-006 | 300 | Static | | |
| 4587-029 | 200 | Cidal | Static | |
| 4587-055 | 300 | Static | | |
| 4587-054 | N/A | | | |
| 4587-054d | N/A | | | |
| 4587-073d | 100 | Cidal | Cidal | Static |
| 4587-0731 | 100 | Cidal | Cidal | Cidal |
| 4587-040 | 100 | Cidal | Cidal | Cidal |
| 4587-074 | N/A | | | |

TABLE 4-continued

FUNGICIDAL ACTIVITY AGAINST C. ALBICANS

| Compound | C. albicans (19 hours) | | | |
|---|---|---|---|---|
| | Lowest | CFU for MFC | | |
| 4587-0561 | 200 | Cidal | Cidal | |
| 4587-060 | N/A | | | |
| 4587-037 | 300 | Cidal | | |
| 4587-065 | N/A | | | |
| 4587-057 | N/A | | | |
| 4587-064 | 100 | Cidal | Cidal | Static |

TABLE 5

FUNGICIDAL ACTIVITY AGAINST A. FUMIGATUS

| Compound | A. fumigatus (48 hours) | | | |
|---|---|---|---|---|
| | Lowest | CFU for MFC | | |
| — | [Active] | 300 | 200 | 100 |
| 4587-006 | N/A | | | |
| 4587-029 | 100 | Cidal | Cidal | Cidal |
| 4587-055 | N/A | | | |
| 4587-054 | N/A | | | |
| 4587-054d | N/A | | | |
| 4587-073d | 100 | Cidal | Cidal | Cidal |
| 4587-0731 | 100 | Cidal | Cidal | Cidal |
| 4587-040 | 100 | Cidal | Cidal | Cidal |
| 4587-074 | N/A | | | |
| 4587-0561 | 100 | Cidal | Cidal | Cidal |
| 4587-060 | 200 | not tested | Cidal | |
| 4587-037 | 200 | Static* | Cidal | |
| 4587-065 | N/A | | | |
| 4587-057 | N/A | | | |
| 4587-064 | 100 | Cidal | Cidal | Cidal |

NOTES FOR TABLES 4-5
MFC = minimum fungicidal concentration
CFU = colony forming units
Cidal = >98% killed
Static = well looked clear, but <98% killed
*colonies were too close together to get a good count. Likely that it was close to being fungicidal.
Note that there appeared to be some kind of precipitate in the 073d and 1 wells. Perhaps the PPT "trapped" the spores. No other compounds showed this PPT.

TABLE 6

COMPARISON OF MOST FUNGICIDALLY ACTIVES

| Compound | C. albicans | | A. fumigatus | |
|---|---|---|---|---|
| | Lowest MIC | Lowest MFC | Lowest MIC | Lowest MFC |
| 4587-002d | 50 | fungistatic | 50 | 50 |
| 4587-0021 | 75 | 100 | 50 | 75 |
| 4587-003 | 50 | 75 | 25 | 25 |
| 4587-056d* | >100 | N/A | 100 | 100 |
| 4587-061 | 50 | 75 | 25 | 25 |
| 4587-062* | 20 | 20 | 10 | 10 |
| 4587-064 | 100 | 100 | 50 | 75 |
| 4587-082 | >100 | N/A | 100 | 100 |
| AMP B | 0.5 | | 2 | |
| Ketaconazole | 32 | | 8 | |

MIC = lowest concentration (ug/mL) that appears to have no growth
MFC = lowest concentration that kills >= 98% of the cells in the well.
Fungistatic = compound with an MIC, but <98% of cells killed
Bold = compound active only in A. fumigatus
Concetration for 062: assume 0.1 mg in 50 uL so final assay concentrations will be ⅕ what was reported. Nevertheless, these concetrations are gross estimates.

The various compounds used in the tests in the above tables are shown below:
Indenopyridine Analogs
RTI-4587-02(d)
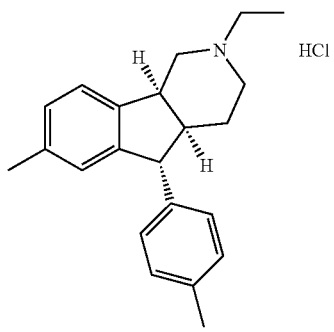
RTI-4587-02(l)
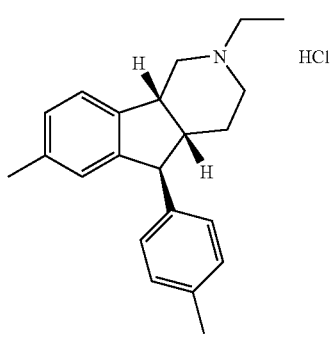
RTI-4587-10
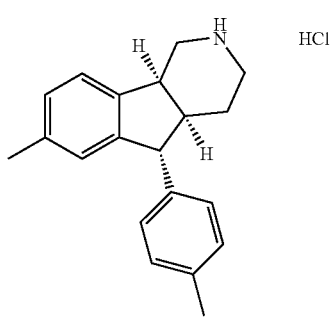
RTI-4587-11
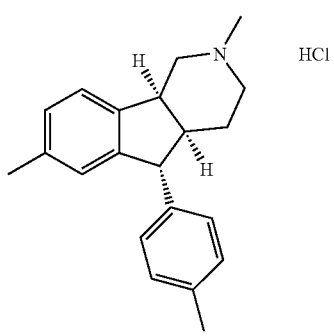
RTI-4587-24
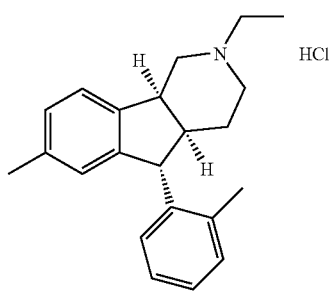
RTI-4587-26
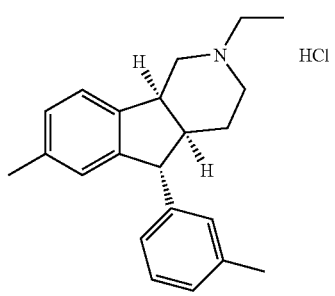
RTI-4587-28
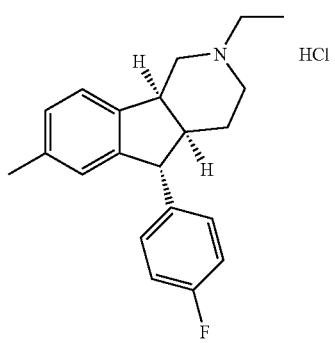
RTI-4587-29
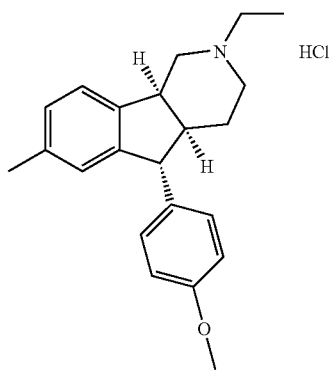
RTI-4587-30
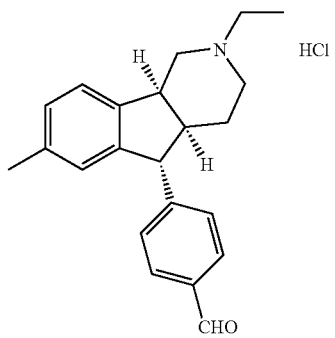

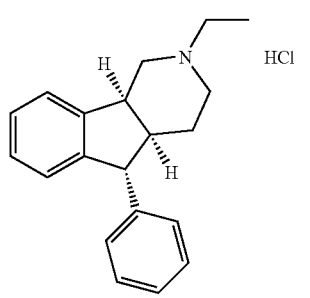
RTI-4587-37
RTI-4587-38
RTI-4587-40
RTI-4587-41
RTI-4587-42
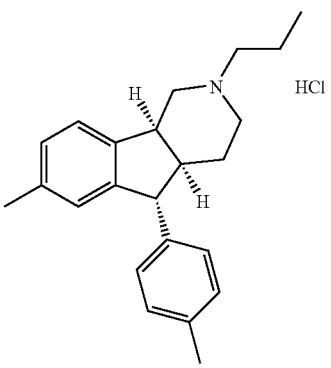
RTI-4587-45
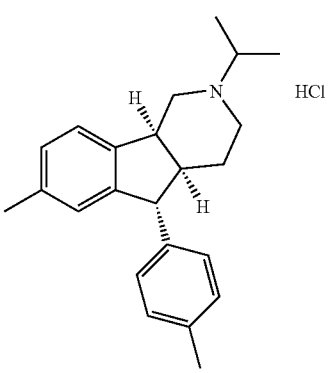
RTI-4587-46
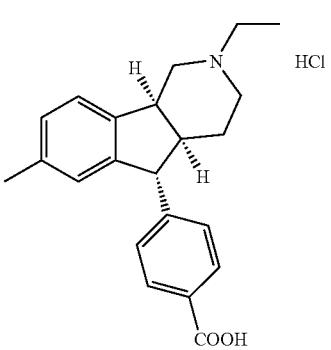
RTI-4587-54
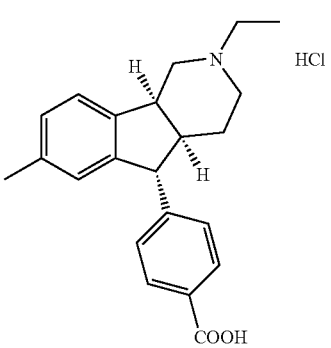
RTI-4587-54(d)

-continued
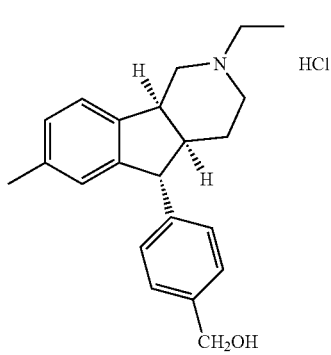
RTI-4587-55
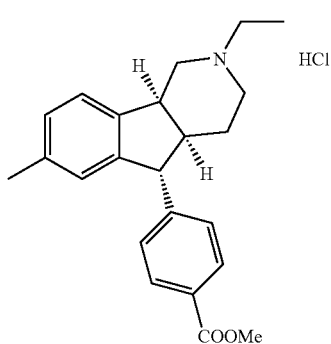
RTI-4587-56(1)
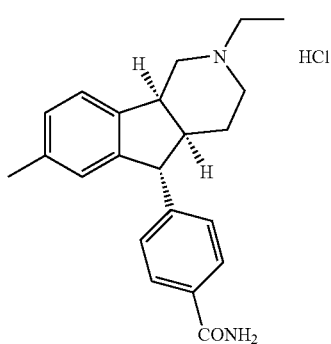
RTI-4587-57
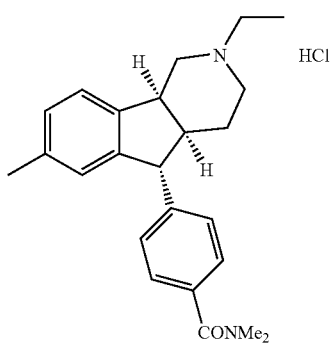
RTI-4587-58
-continued
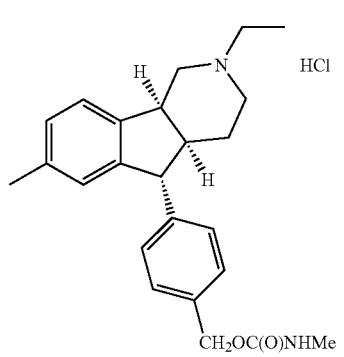
RTI-4587-59
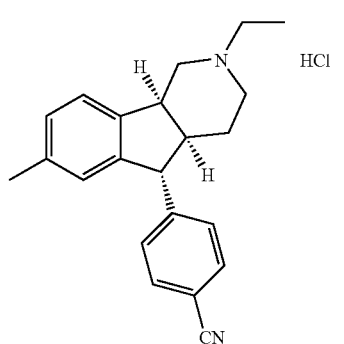
RTI-4587-60
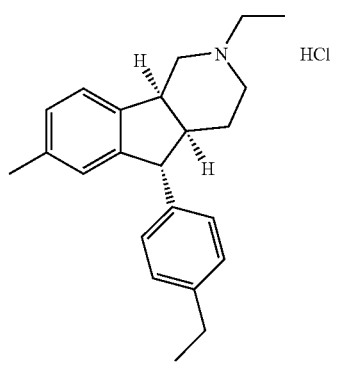
RTI-4587-61
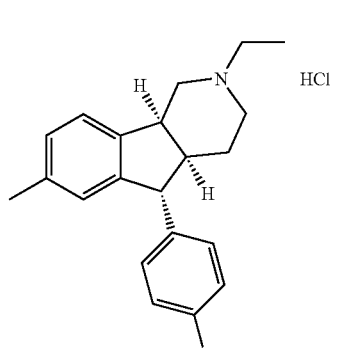
RTI-4587-62

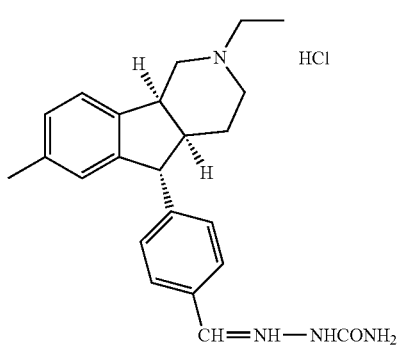
RTI-4587-63
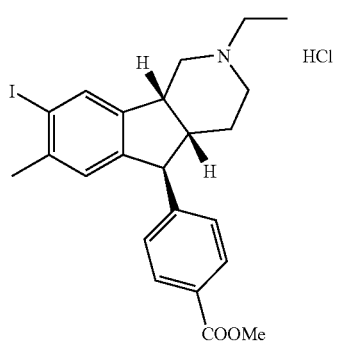
RTI-4587-73(d)
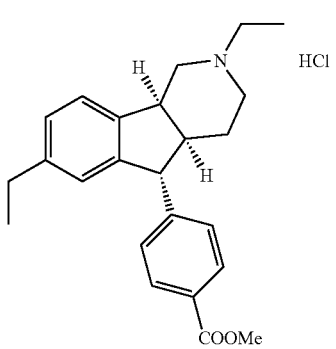
RTI-4587-64
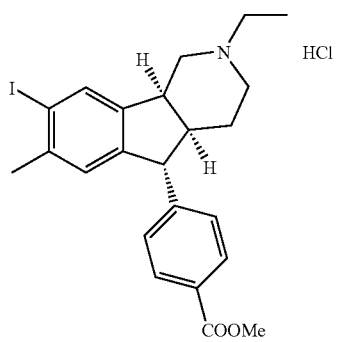
RTI-4587-73(l)
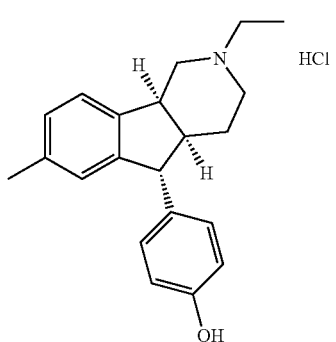
RTI-4587-65
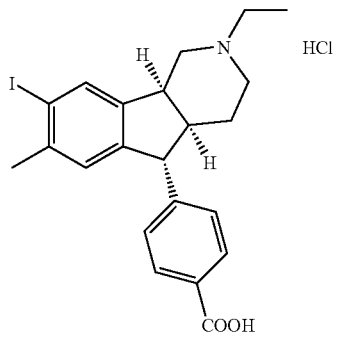
RTI-4587-74
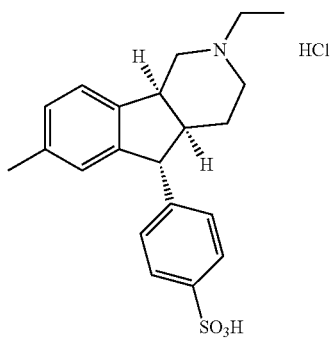
RTI-4587-68
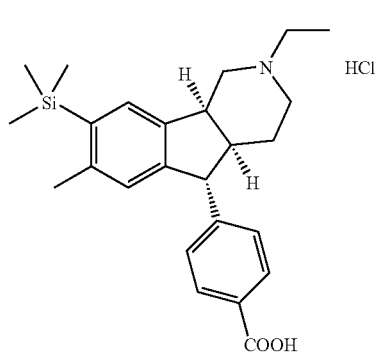
RTI-4587-75

RTI-4587-76
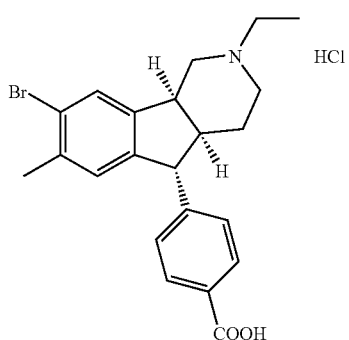
RTI-4587-77
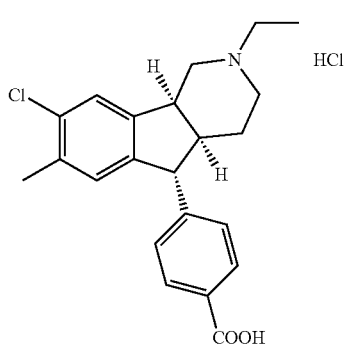
RTI-4587-78
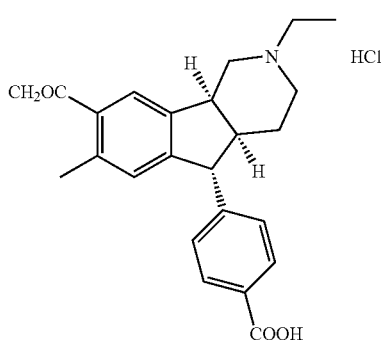
RTI-4587-79
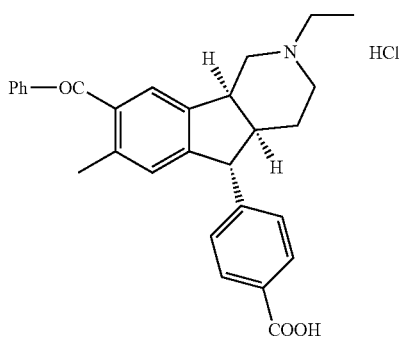
RTI-4587-80
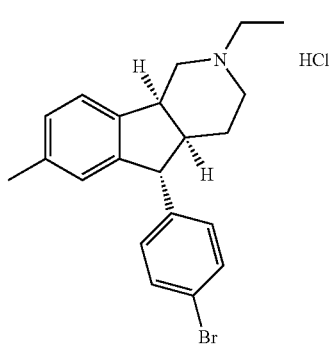
RTI-4587-003
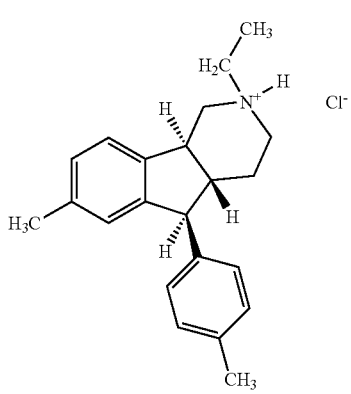
(Relative stereochemistry)
RTI-4587-002
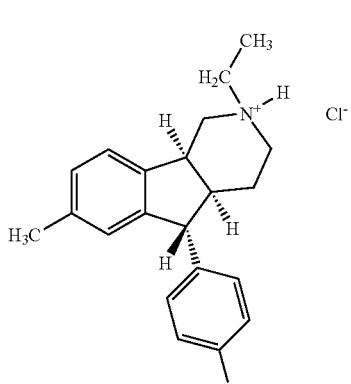
(Relative stereochemistry)
RTI-4587-006
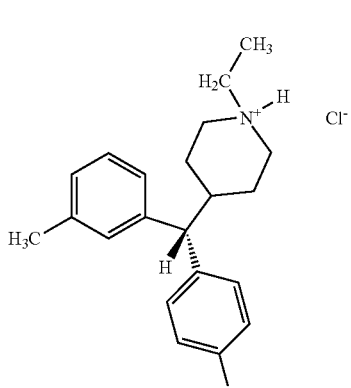
RTI-4587-006
(Relative stereochemistry)

-continued

RTI-4587-082

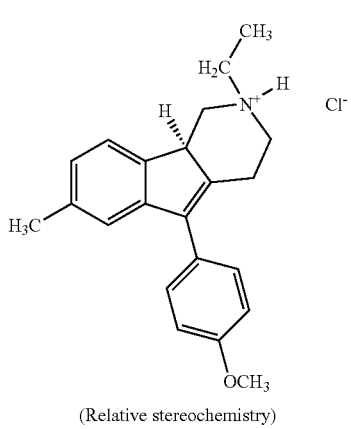

(Relative stereochemistry)

Precursors for the compounds of the invention can be prepared by the method disclosed in U.S. Pat. No. 5,319,084 using modifications of the method disclosed in U.S. Pat. No. 3,678,057. These patents are incorporated herein by reference in their entirety. The $R^3$ substituents are introduced into the molecule by using an appropriate Grignard reagent or phenyl lithium reagent. The mixtures of enantiomers produced by this process are resolved into pure enantiomers by salt formation followed by selective crystallization or chromatography. For example, resolution of compound 1 can be effected by salt formation with S(+) and R(−)-2,2'-(1,1'-binaphthyl) phosphoric acid and resolution of compound 3 can be effected by salt formation with R- and S-mandelic acid as described in C. E. Cook et al, J. Med. Chem., 38:753 (1995). Optical purity is established by high pressure liquid chromatography (HPLC) on a CHIRACEL-OD column.

Compounds of this invention may be prepared beginning with carboxylic acid 2 or one of its esters (for example, 3). Compounds such as 2 and 3 are prepared as described in U.S. Pat. No. 5,319,084. Alternatively, they may be made by the process shown in FIG. 2, where an N-substituted-3-aryl-hexahydropyridine-4-carboxylic acid ester (4) is hydrolyzed to carboxylic acid 5, which is then treated with thionyl chloride to yield acid chloride 6. Treatment of this compound with $AlCl_3$ cyclizes the compound to the tricyclic ketone 7. Reaction of ketone 7 with a p-halogen-substituted phenyl magneseum halide or p-halogen-substituted phenyl lithium (4-bromophenyl lithium) forms tertiary alcohol 8, which upon treatment with a trialkylsilane, for example a tri-$C_{1-6}$ alkyl silane such as triethylsilane and $BF_3$ is reduced to compound 9, which is then refluxed with a strong base (e.g. KOH) in an alcohol solvent, preferably high boiling, such as n-butanol to yield bromophenyl compound 10 having the desired stereochemistry. Conversion of the bromophenyl group to a lithiophenyl group, for example with a $C_{1-6}$ alkyl Li compound, and carboxylation ($CO_2$) using known reagents yields carboxylic acid 2, which may be esterified by conventional means well known in the art, for example reaction with a $C_{1-6}$ alkanol, to obtain ester 3.

Figure 2:
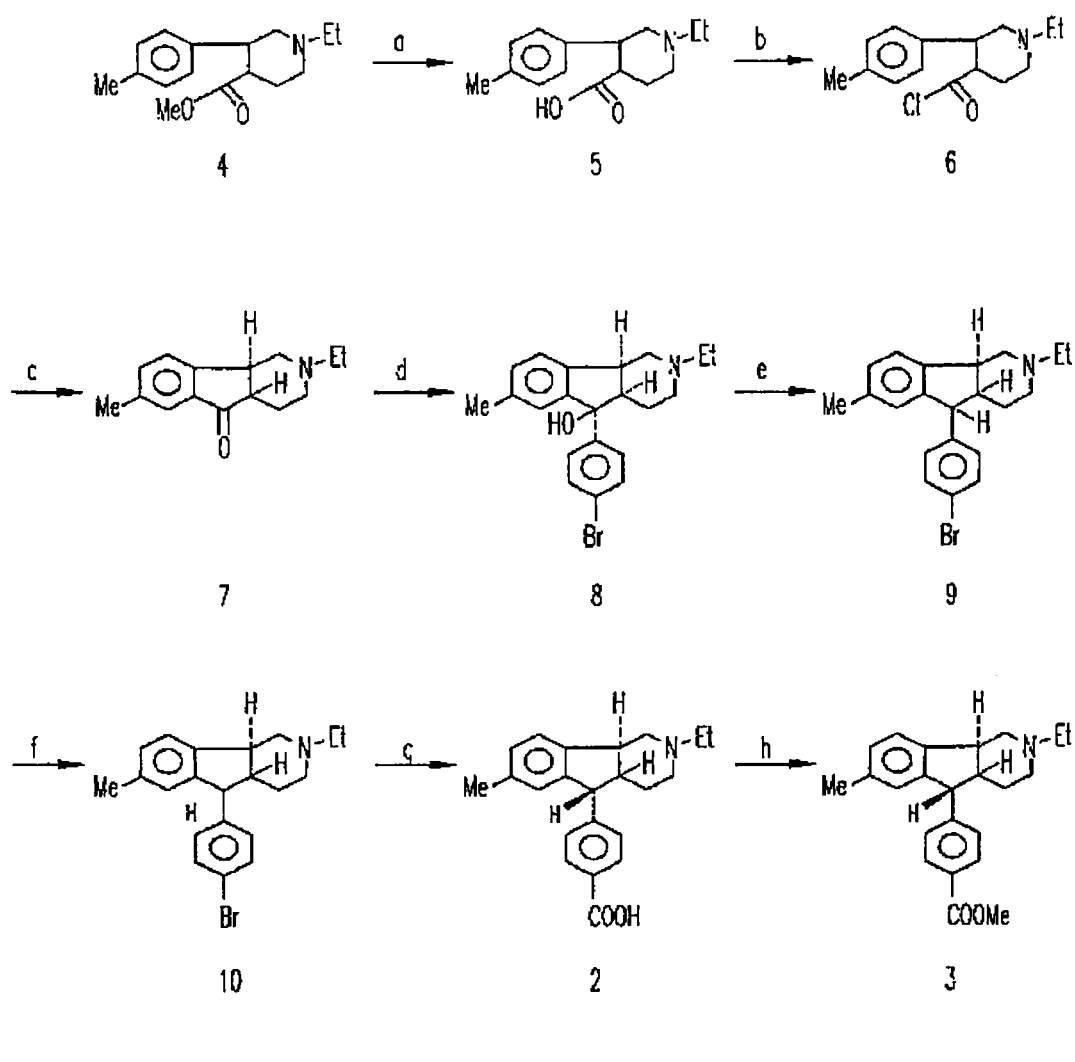
FIG. 2 shows a process for preparing precursors of the compounds of the present invention.
Figure 3:
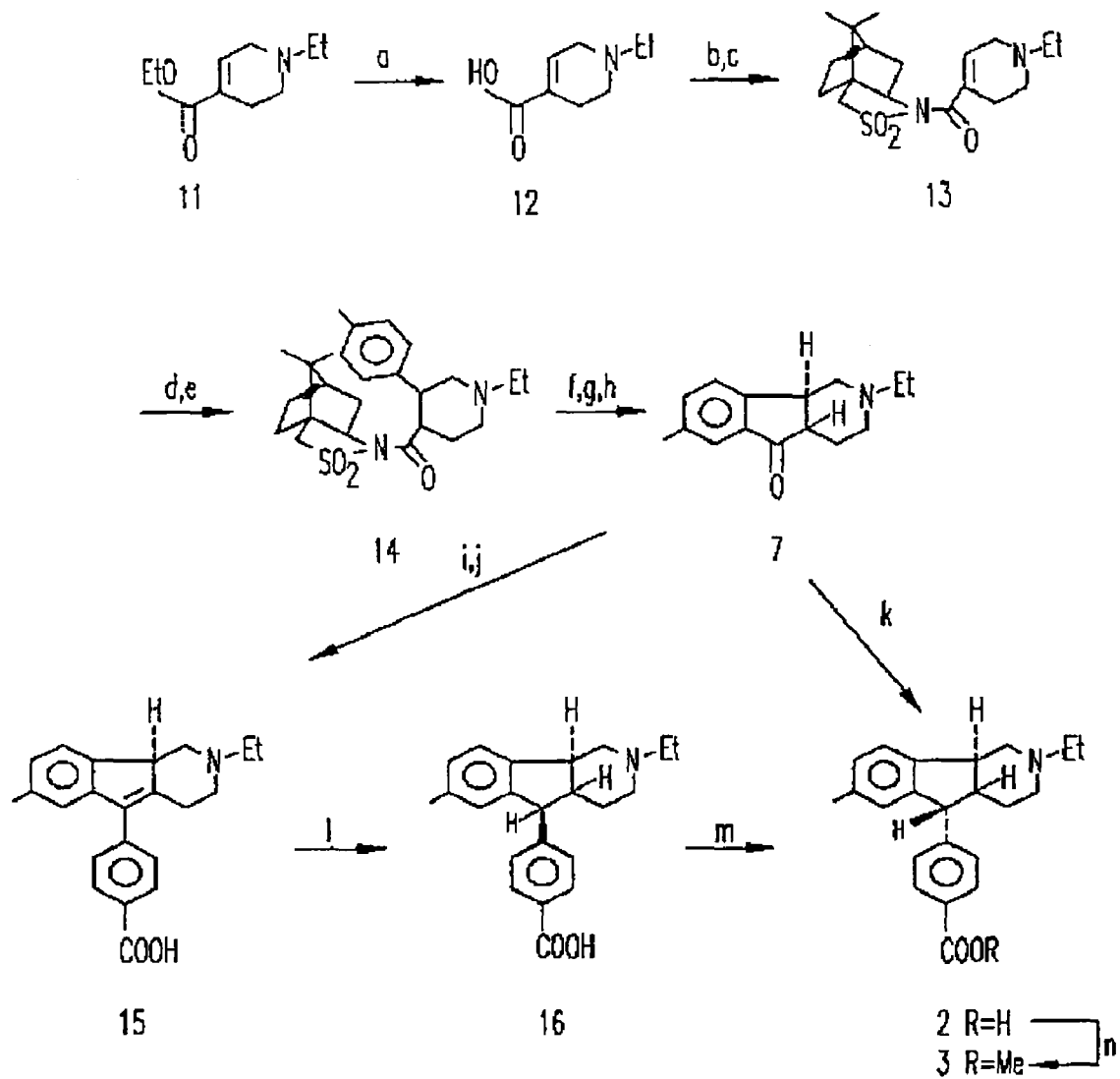
FIG. 3 shows an enantioselective synthesis of precursor compounds to the compounds of the invention.

The synthesis noted above may be modified to provide an enantioselective synthesis of the active enantiomers of compounds 2 and 3, which may then be used to synthesize the active enantiomers of the present invention as shown in FIG. 3. Thus, an N-substituted 1,2,5,6-tetrahydropyridine-4-carboxylic acid (for example, 12) is converted to its acid chloride and the latter compound is used to acylate 1R(+)-(2,10)-camphorsultam or 1S(−)-(2,10)-camphorsultam. When the resulting enoylsultam (13) is treated with an aryl magnesium halide it undergoes 1,4-addition with high diastereofacial selectivity to introduce an aryl group at the 3-position in high enantiomeric excess. Crystallization yields pure enantiomer 14. The amide function is hydrolyzed and the chiral adjuvant may then be recovered. The carboxylic acid is then converted to tricyclic ketone 7 as described above. This compound can be converted to essentially enantiomerically pure 2 and 3 by treatment with bromophenyl lithium and subsequent steps as shown in FIG. 2. Alternatively, chiral ketone 7 may be converted to an enantiomerically enriched 2 and 3 by the procedure described for synthesis of racemates in U.S. Pat. No. 5,319,084. The degree of enrichment is dependent upon catalyst and temperature in the reduction of the enantiomeric tetrahydroindeno pyridine analogous to intermediate 5. See FIG. 3 of U.S. Pat. No. 5,319,084. Thus, there was 73% enantiomeric excess (ee) at 23° C. with $PdCl_2/NaBH_4/3$ atm $H_2$, but complete racemization at 55° C.; whereas with Pt/c/$H_2$ the ee at 60° C. was comparable to that at 23° C. (67% and 70%, respectively).

Figure 4:
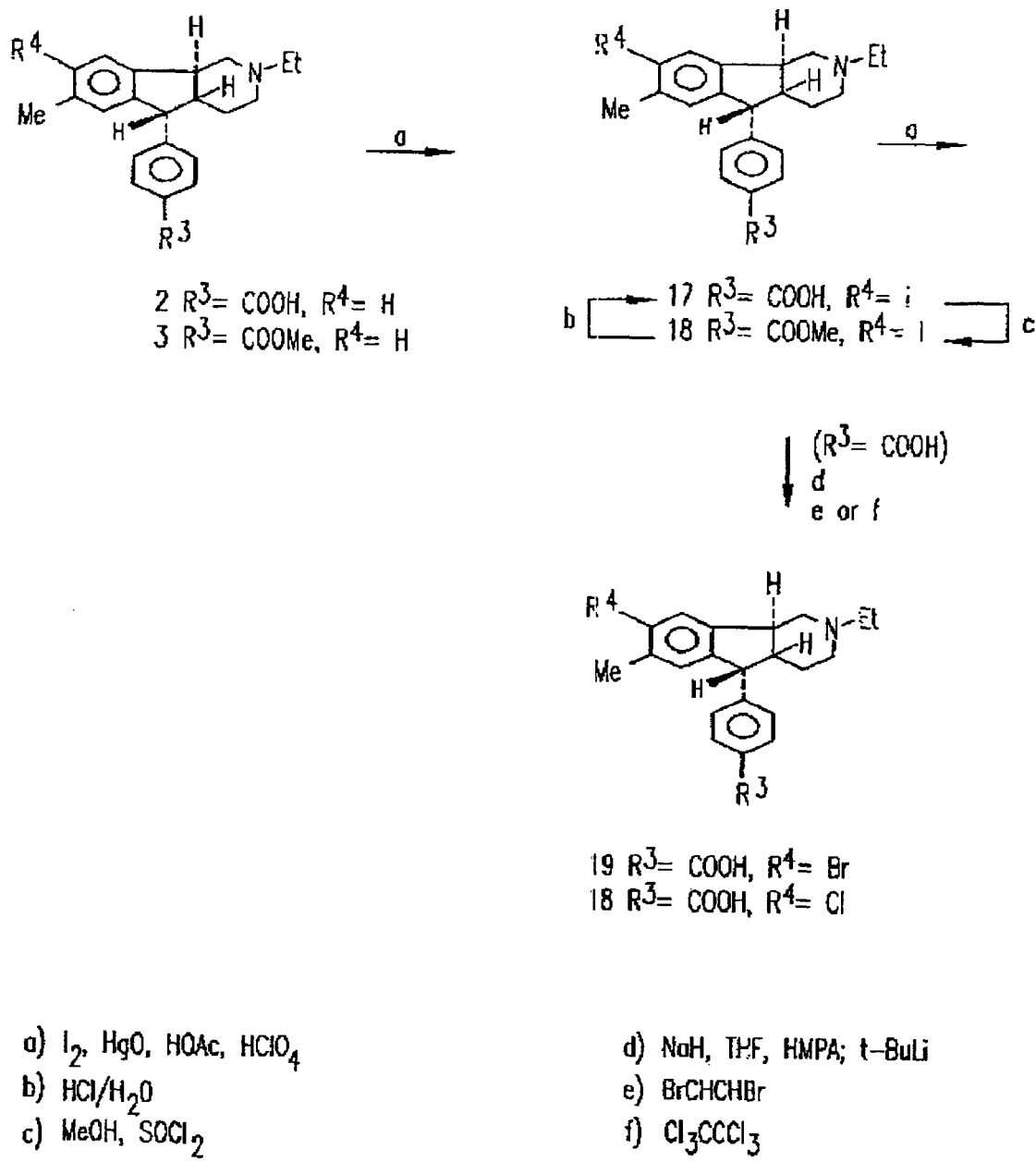
FIG. 4 shows a synthetic scheme for iodinating the precursor compounds prepared as shown in FIGS. 2 and 3 and the conversion of the iodo compounds to additional compounds within the scope of the invention.

Either carboxylic acid 2 or its esters, such as methylester 3, may be iodinated to yield the 8-iodo analogs 17 or 18 by reaction with iodine under oxidizing conditions or with an oxidized form of iodine (FIG. 4). For example, reaction of 3 with about 1 mol of iodine in the presence of mercuric oxide leads in high yield to 8-iodo compound 18. The ester and acid are interconvertible by standard chemical techniques well known in the art. Either the racemates or enantiomers may be used. One may also use a radioactive isotope of iodine, such as $^{125}I$, $^{123}I$ or $^{131}I$ to yield a radio-labeled analog of 17 or 18. Such compounds are useful for determining the localization and site of action of these compounds and may be used as imaging agents for diagnosis of male reproductive disorders.

The iodo compounds, in particulars the 8-iodo acid 17, may be converted to the bromo and chloro compounds by formation of a metal salt of the acid, for example, the sodium salt, and then by formation of an 8-metal intermediate where the metal is a metal such as lithium or a substituted metal with known reagents such as t-BuLi. Reaction of the 8-metal intermediate with a halogen source such as hexachloroethane or 1,2-dibromoethylene leads to the corresponding 8-substituted analogs, such as compounds 19 or 20 shown in FIG. 4. The corresponding fluoro compounds can be prepared by reacting the 8-metal intermediate with chlorotrimethylsilane to form the corresponding 8-trimethylsilyl compound and then reacting this compound with lead tetra-acetate in the presence of $BF_3$-$Et_2O$, See De Mio et al, 1993, Tetrahedron, 49:8129-8138.

One may obtain radioactive analogs of the various subject compounds by, for example, treating the 8-metal intermediate with a reagent containing an electrophilic halogen atom as its radioactive isotope or, as pointed out earlier, one can make the radioactive analogs of compounds 17 or 18 by substituting a radioactive isotope of iodine in the synthesis of the compounds described above. Tritium-labeled compound of the invention may be obtained, for example, by reduction of the 8-iodo compounds with tritium gas catalyzed by a noble metal, such as palladium or platinum. Carbon-14 analogs may be made, for example, by using $^{14}C$ labeled carbon dioxide in step "g" of the synthesis of compound 2 as shown in FIG. 2. Other methods for isotopic labeling of the compounds commonly used in the art of radiochemical synthesis may also be applied.

The compounds of the present invention are useful as male antifertility drugs for controlling fertility in mammals, including humans. In addition to their potential use in family planning, the compounds of the invention are also useful to control fertility in domestic, wild or feral animals, where lethal measures are not practical or desirable. For example, the control of deer populations is a problem in some areas of the United States. Oral administration of the compounds of the present invention to seasonal breeding animals such as deer by means of baited feed containing these compounds at appropriate times would substantially reduce reproductive capacity. Other target animals include rodents such as mice, rats, prairie dogs, etc., as well as feral goats, swine, horses, etc. Administration of the compounds of this invention to captive zoo animals provides a means of controlling reproduction in species which become overpopulated.

By "controlling fertility" as used herein is meant reducing the reproductive capacity or fertility of the mammal treated. The length of infertility is a function of dose such that with sufficient doses one may extend the period of infertility so as to essentially use the compounds of this invention to perform sterilization; thus, the compounds of the invention may replace surgical vasectomy as a means of male sterilization. When performing such sterilization, the compounds of the invention are administered in a single dose or a plurality (two or more) of doses where the doses are sufficient to reduce the sperm producing ability of the mammal (spermatogenic index) to a level of infertility. That is, the compounds of the invention are administered in an amount and for a length of time sufficient to reduce the sperm count to a level which is not sufficient to reproduce.

For the above-mentioned uses, the dose of the compound of the invention will naturally vary depending on the specific compound employed, the mode of administration and the length of infertility desired. However, satisfactory results are obtained in animals at oral doses from about 0.02 to about 10 mg/kg, preferably about 0.1-3 mg/kg body weight per day. For larger animals, a daily dose amount of about 10-100 mg may be administered as a single oral unit dose or in divided dosage units containing about 0.1-10 mg of the compound of the present invention. When administering a single active enantiomer, one may generally administer a smaller dose then when administering a racemic compound. If desired or necessary, the compounds of the invention may be administered together with solid or liquid carriers or diluents or in slow-release form. Formulation of these pharmaceuticals forms is well known in the art and any conventional method of preparing solid, liquid and slow-release formulations may be used with the compounds of the present invention. The compounds of the invention may also be administered by means of conventional implants or skin patches which are well known in the art.

The compounds of the invention may be used in human contraception in males, either by reversibly blocking spermatogenesis or in nonsurgical sterilization. In the latter use, administration of appropriately large doses realizes the effects of vasectomy without the use of surgery and with the elimination of potential side effects of vasectomy.

The compounds of the invention are also useful in the control of reproduction in domestic, wild, feral or zoo animals For example, the compounds may be in the control of reproduction in zoo animals. Wild and feral animal populations close to human habitation, for example deer, or animal populations which strongly impact the natural ecology, for example wild mustangs and feral hogs, may be controlled by selectively baiting without using lethal means such as shooting or poisoning. Animal behavior is not affected in this process, only fertility.

When $R^4$ is a radioactive label, the compounds of the invention are useful to study testicular function and diagnose testicular malfunction. Administration of the compounds in the dosages noted above binds to testicular tissue.

In their anti-spermatogenic properties, the high degree of chemo-, stereo- and enantioselectivity of the compounds together with their lack of general effects, such as on libido, indicates that they are interacting with a specific macromolecule in the testis. Treatment of testis or testis fractions with a radioactive derivative of the compounds followed by detection of radioactivity by techniques well known in the art of radiochemistry enable one to locate and identify the portion of the testis and the macromolecule involved in the antispermatogenic effect. This may be used to detect and identify an important constituent of the testis, disruption of which can lead to an antifertility effect. Comparison of the ability of other compounds (such as analogs of the current compounds or those from combinatorial libraries) to inhibit the binding of the radiolabeled compound can lead to even more selective and potent antispermatogenic compounds. Furthermore, by administering a small dose (too small to have a clinical effect on fertility) of the radiolabeled compound to an animal or human subject and then measuring the amount of radioactivity in the testis or specific areas of the testis, one can show whether an existing problem of infertility is related to the lack of this macromolecule. The radioactivity can be measured in a living animal or human by techniques such as PET and SPECT which are well known in the art of imaging of biological tissues.

The compounds are also useful as internal standards for analytical purposes. Thus for example a compound such as 20 may be added in known quantity to a sample of blood, plasma or tissue from an animal or human dosed with compound 17. The sample of blood, plasma or tissue may then be extracted with an organic solvent and the extract subjected to analytical high performance liquid chromatography or to gas chromatography, either with or without conversion to a derivative such as the methyl ester. Measurement of the areas of the chromatographic peaks associated with 17 and 20 and comparison to the area ratios of known amounts of 17 and 20 subjected to the same conditions enable one to determine the concentration of 17 in the sample of blood, plasma or tissue. Because of the close structural resemblance between 17 and 20, the physicochemical properties of the two compounds will be similar for extraction, thus making one an almost ideal standard for the other.

For use as a spermicide, the compounds of the present invention can be prepared in a variety of forms for administration. Conventional spermicidal composition forms are readily prepared using known methods. Such spermicidal compositions can take the form of gels, foams, jellys, creams, ointments, salves, etc. Conventional carriers are used to prepare the compositions. The present spermicidal compositions can be administered alone or in combination with one or more barrier methods of contraception, such as a diaphragm, sponge or condom. The composition can be applied directly to the diaphragm, sponge or condom immediately prior to use, or can be prepackaged along with the sponge or condom (or even diaphragm, although most diaphragms are for multiple uses and are cleaned between uses).

For use as a fungicide, the composition of the present invention can be prepared in any suitable form for administration to the area in need thereof. The forms of administration include, but are not limited to, those listed above for spermicidal compositions, as well as liquid mixtures. It is also possible for the fungicidal and spermicidal properties to be used in combination using one of the common forms of administration.

Other features of the present invention will become apparent in the course of the following descriptions of exemplary embodiments which are given for illustration of the invention and are not intended to be limiting thereof.

EXAMPLES

Example 1

Synthesis of (4aRS,5SR,96RS)2-Ethyl-7-methyl-2,3, 4,4a,5,9b-hexahydro-5-(p-carboxyphenyl-1H-indeno [1,2-c]pyridine Hydrochloride Iodoethane (540 g, 3.41 mol) in methanol (500 mL) was added to ethyl isonicotinate (500 g, 3.31 mol). The mixture was refluxed gently overnight. Sodium borohydride (140 g) was added portionwise to the above solution under cooling (ice bath). After the addition of NaBH$_4$ was complete, the mixture was stirred at room temperature overnight. Most of the methanol was evaporated, water and ether were added to the solution and ether layer was separated. Evaporation of dry ether (Na$_2$SO$_4$) layer gave an oil. Distillation of this red oil gave a yellowish oil 470 g, 78%): bp 160° C. at 0.5 mm.

The above compound (146 g, 0.8 mol) in dry ether (200 mL) was added dropwise to 1M p-tolylmagnesium bromide in ether (600 mL, 1.6 mol at −10° C.). After being stirred for 3 h, the reaction mixture was poured into 10% aqueous NH$_4$Cl solution (200 mL). The aqueous layer was extracted with ether. Evaporation of the dry (Na$_2$SO$_4$) ether layer gave a yellowish brown oil. This oil was dissolved in 18% aqueous HCl (500 mL) and extracted with ether. The aqueous HCl solution was refluxed for 2 h. Evaporation of the solvent gave the corresponding amino acid (181 g, yield 80%), which (32 g) was mixed with polyphosphoric acid (500 g) and stirred vigorously at 140° C. for 3 h. The reaction mixture was cooled and 50% KOH aqueous solution was added cautiously. The basified solution was extracted with ether. Evaporation of the dry (Na$_2$SO$_4$) ether layer gave 2-ethyl-7-methyl-2,3,4,4a.alpha., 5,9b.alpha.-hexahydro-1H-indeno[1,2-c]pyridin-5-one as an oil (22.6 g, 87%). An analytical sample was obtained by passing through a small column of SiO$_2$ using a gradient of MeOH in CHCl$_3$ (0-5%): $^1$H NMR (90 MHZ, CDCl$_3$) δ7.5 (1H, s, H-6), 7.3 (2H, m, H-8, H-9), 3.5 (1H, m), 3.0 (1H, m), 2.6 (2H, m), 2.3 (3H, s, 7-Me), 2.2 (3H, m), 1.9-1.7 (3H, m), 1.1 (3H, t, Me); HRMS (M+): Calcd. for C$_{15}$H$_{19}$NO: m/z 229.1467. Found: m/z 229.1466.

To a mechanically stirred solution of para-bromobenzoic acid (1.6 g, 8.0 mmol) in tetrahydrofuran (THF) (15 mL) at −78° C. was added n-butyllithium (16.2 mmol, 6 mL of a 2.5M solution in hexane) dropwise over a 45 min period. After the mixture was stirred for an additional 1.5 h, the tricyclic ketone (1.1 g, 5.1 mmol) was added as a solution in THF (5 mL) dropwise over a 30 min period and stirring was continued for 2.5 h at −78° C. The mixture was poured into ice cold 1M HCl (75 mL) and extracted with ether (2.times.30 mL). The acidic aqueous layer was stirred for 15 h at room temperature and concentrated under reduced pressure to afford a solid. This solid was purified via flash column chromatography on silica with a gradient elution of 10-20% MeOH in CHCl$_3$ and yielded 2-ethyl-7-methyl-2,3,4,9b-tetrahydro-5-(p-carboxyphenyl)-1H-indeno[1,2-c]pyridine hydrochloride as a yellow solid (1.1 g, 58%).sup.1H NMR (250 MHZ, CDCl$_3$), δ1.54 (3H, t, J=7.2 Hz), 2.35 (3H, bs), 2.25-2.42 (1H, m), 2.50-2.72 (1H, m), 2.94-3.0 (1H, m), 3.15-3.30 (2H, m), 3.50-3.80 (2H, m), 4.17-4.30 (1H, m), 4.40-4.52 (1H, m), 7.0-7.12 (2H, m), 7.32 (1H, d, J=7.5 Hz), 7.45 (2H, d, J=8.4 Hz), 8.20 (2H, d, J=8.4 Hz). HRMS (M+) Calcd. MW for C$_{22}$H$_{23}$NO$_2$: m/z 333.1729. Found: m/z 333.1725.

To a solution of the above compound (379 mg, 1.03 mmol) in ethanol/water (40 mL of a 1:1 mixture) was added NaCl (81 mg), PdCl$_2$ (98 mg), NaBH$_4$ (100 mg), and concentrated HCl (10 drops). After the mixture was shaken on a Parr apparatus under a hydrogen atmosphere (45 psi) at 50° C. for 15 h, it was filtered through Celite and concentrated under reduced pressure. The resulting solid was suspended in absolute ethanol, filtered through Celite, and the filtrate was concentrated under reduced pressure to yield (4aRS,5RS,9bRS)2-ethyl-7-methyl-2,3,4,4a,5,9b-hexahydro-5-(p-carboxyphenyl)-1H-indeno[1,2-c]pyridine hydrochloride. $^1$H NMR (250 MHZ, CDCl$_3$): δ1.4 (3H, t, 7.2 Hz), 1.50-1.60 (1H, m), 1.85-2.00 (1H, m), 2.20 (3H, s), 2.20-2.40 (1H, m), 2.70-2.90 (3H, m) 2.90-3.15 (2H, m), 3.50-3.65 (1H, m), 3.90-4.10 (1H, m), 4.50 (1H, d, J=7.3 Hz), 6.95, (1H, bs), 7.10 (1H, d, J=7.5 Hz), 7.20 (1H, d, J=7.5 Hz), 7.30, (2H, d, J=8.0 Hz), 8.00 (2H, d, J=8.0 Hz). HRMS (M+) Calcd. MW for C$_{22}$H$_{25}$NO$_2$: m/z 335.18853. Found: m/z 335.1887.

To a solution of potassium hydroxide (15 g) in n-butanol (60 mL) was added the above compound (2.99 g, 8.0 mmol) in one portion. After being refluxed for 20 h, the dark brown mixture was cooled to 0° C. and acidified to pH=1 with 18% HCl. The solvent was removed in vacuo to afford a yellow solid. This solid was taken up in CHCl$_3$, filtered through Celite, and the filtrate was concentrated in vacuo to afford crude (4aRS,5SR,9bRS)-2-ethyl-7-methyl-2,3,4,4a,5,9b-hexahydro-5-(p-carboxyphenyl)-1H-indeno[2,2-c]pyridine hydrochloride as an off-white solid. This solid was purified via flash column chromatography using 10% MeOH—CHCl$_3$ and yielded 1.23 g (41%) of the title compound as a white solid. m.p.=280° C. (dec.) $^1$H NMR (250 MHZ, CDCl$_3$—CD$_3$OD). δ1.45 (3H, t, J=7.3 Hz), 1.8 (1H, bd, J=14.7 Hz), 2.2 (3H, s), 2.4-2.7 (2H, m), 3.0-3.4 (4H, m), 3.4-3.7 (2H, m), 3.7-4.0 (1H, m), 4.2 (1H, d, 11 Hz), 6.6 (1H, bs), 7.0-7.2 (4H, m), 8.0 (1H, d, J=7.7 Hz). HRMS (M+) Calcd. MW for C$_{22}$H$_{25}$NO$_2$: m/z 335.18853. Found: m/z 335.18830.

Anal. Calcd. for C$_{22}$H$_{26}$ClNO$_2$·½H$_2$O: C, 69.37; H, 7.14; N, 3.68. Found: C, 69.72; H, 7.15; N, 3.55.

Example 2

(4aRS,5SR,9bRS)-2-Ethyl-7-methyl-2,3,4,4a,5,9b-hexahydro-5-(p-carbomethoxyphenyl)-1H-indeno[1,2-c]pyridine Hydrochloride To a solution of the carboxylic acid of Example 1 (3.6 g, 9.69 mmol) in methanol (50 mL) at −10° C. was added thionyl chloride (1.1 mL, 14.5 mmol) over a 10 min period. The resulting solution was allowed to stand in a refrigerator at 5° C. for 68 h during which time the product had begun to crystallize out as fine white needles. Three crops were obtained and combined to yield 2.65 g of the title compound. mp=204° C. (sublimed). $^1$H NMR (250 MHz, CDCl$_3$): δ1.1 (3H, t, J=7.2 Hz), 1.6 (1H, bd, J=14.2 Hz), 1.80-2.00 (2H, m), 2.1-2.2 (1H, m), 2.2 (3H, s), 2.4 (2H, q, J=7.2 Hz), 2.5-2.6 (1H, m), 2.7-2.8 (1H, m), 2.9 (1H, dd, J=5.94, 11.64 Hz), 3.3-3.4 (1H, m), 3.9 (3H, s), 4.2 (1H, d, J=10.0 Hz), 6.7 (1H, bs), 7.0 (1H, d, J=7.5 Hz), 7.2 (1H, d, J=7.5 Hz), 7.3 (2H, d, J=8.0 Hz), 8.0 (2H, d, 8.0 Hz).

Anal. Calcd. for C$_{23}$H$_{28}$ClNO$_2$·¼H$_2$O: C, 70.75; H, 7.36; N, 3.59. Found: C, 70.67; H, 7.36; N, 3.59.

Example 3

Synthesis of (4aRS,5SR,9bRS)-2-Ethyl-2,3,4,4a,5, 9b-hexahydro-8-iodo-7-methyl-5-(4-carbomethoxyphenyl)-1H-indeno[1,2-c]pyridine Hydrochloride (18) and its (1)-enantiomer ((1)-18)

To a stirring solution of (4aRS,5SR,9bRS)-2-ethyl-2,3,4, 4a,5,9b-hexahydro-7-methyl-5-(4-carbomethoxy phenyl)-1H-indeno[1,2-c]pyridine (341 mg, 0.88 mmol) in glacial acetic acid (2 mL) was added 62% $HClO_4$ (1 mL) followed by HgO (205 mg, 0.95 mmol). The mixture was briefly sonicated in order to effect a homogenous solution. A solution of iodine (235 mg, 0.925 mmol) in glacial acetic acid (17 mL) was added dropwise over 15 min and the resulting mixture was stirred at room temperature overnight. The orange-red mixture was poured into water (100 mL), cooled to 5° C., basified to pH 12 with 30% NaOH, and extracted with ether (3×75 mL). The clear, colorless ether extracts were combined, washed successively with water (20 mL) and brine (30 mL), dried ($MgSO_4$), filtered, and concentrated in vacuo to afford the crude free base of 18 (448 mg). This material was transformed into the HCl salt using 3% methanolic hydrogen chloride and recrystallized from EtOAc-MeOH. Yield=400 mg (89%). m.p.=>190° C. (dec.). $^1$H NMR (250 MHz, $CDCl_3$, as free base);δ1.15 (3H, t, J=7.2 Hz), 1.65 (1H, bd), 1.8-2.1 (3H,m), 2.32 (3H, s), 2.48 (3H, q, J=7.2 Hz, +m), 2.80 (1H, bd), 2.97 (1H, dd, J=11.8, 5.8 Hz), 3.41 (1H, m), 3.91 (3H, s), 4.19 (1H, d, J=9.8 Hz), 6.78 (1H, s), 7.22 (2H, d, J=8.3 Hz), 7.73 (1H, s), 8.00 (2H, d, J=8.3 Hz). HRMS: Calcd. for $C_{23}H_{26}NO_2I$, (corresponding to the free base): m/z 475.1008. Found: m/z 475.1004.

Anal. Calcd. for $C_{23}H_{27}ClINO_2 \cdot \frac{1}{2}H_2O$: C, 53.04; H, 5.42; N, 2.69. Found: C, 52.70; H, 5.60; N, 2.57. The active enantiomer, (1)-18, was synthesized in a similar fashion starting from (1)-3. $[\alpha]_D=-5.6$ (c=1.18, $CHCl_3$).

Example 4

Synthesis of (4aRS,5SR,9bRS)-2-Ethyl-2,3,4,4a,5, 9b-hexahydro-8-iodo-7-methyl-5-(4-carboxyphenyl)-1H-indeno[1,2-c]pyridine Hydrochloride (17)

To (4aRS,5SR,9bRS)-2-Ethyl-2,3,4,4a,5,9b-hexahydro-7-methyl-5-(4-carboxyphenyl)-1H-indeno[1,2-c]pyridine hydrochloride (250 mg, 0.673 mmol) in 2 mL of acetic acid was added 6 mL of a 1:1 mixture of acetic acid and perchloric acid. HgO (1.35 mmol) was added and the reaction mixture was stirred at room temperature until the HgO dissolved. A solution of $I_2$ (427 mg, 1.68 mmol) in 4 mL of acetic acid and 6 mL of $CH_2Cl_2$ was added dropwise to the reaction mixture by addition funnel. The reaction mixture was stirred overnight at room temperature and then filtered through celite. The red solid was washed with water and $CH_2Cl_2$. The combined biphasic filtrate was separated by separatory funnel. The organic phase was washed with saturated sodium bisulfite solution, dried over sodium sulfate (anhydrous), filtered and concentrated to give 234 mg of yellow brown solid, converted to the hydrochloride in the usual way. $^1$H NMR (250 MHz, $CDCl_3/CD_3OH$) δ1.28 (3H, t, J=7.2 Hz), 2.0-2.1 (1H, m), 2.3 (3H, s), 2.56 (2H, m), 3.04 (3H, m), 3.24 (1H, m), 3.46 (2H, m), 4.18 (1H, d, J=11 Hz), 6.73 (1H, s), 7.13 (2H, d, J=8.2 Hz), 7.71 (1H, s), 7.89 (2H, d, J=8.2 Hz). HRMS Calcd for $C_{22}H_{24}NO_2I$ (corresponding to the free base): m/z 461.0852. Found: m/z 461.0857.

Example 5

Synthesis of (4aRS,5SR,9bRS)-2-Ethyl-8-Bromo-7-Methyl-2,3,4,4a,5,9b-Hexahydro-5-(4-carboxyphenyl)-1H-Indeno[1,2-c]pyridine Hydrochloride (19)

(4aRS,5SR,9bRS)-2-Ethyl-8-iodo-7-methyl-2,3,4,4a,5, 9b-hexahydro-5-(4-carboxylphenyl)-1H-indeno[1,2-c]pyridine hydrochloride (200 mg, 0.402 mmol) was dissolved in 20 mL THF and 0.4 mL hexamethylphosphoramide. To this solution was added 50 mg sodium hydride (60% in mineral oil). The mixture was refluxed for 1 h and then cooled to −78° C. Tert-Butyllithium solution (0.73 mL, 1.1 M in pentane, 0.804 mmol) was added slowly. After the addition the mixture was stirred at −78° C. for 20 min. 1,2-Dibromoethylene (1 mL) was added. The mixture was stirred at −78° C. for another 30 min and then warmed to room temperature. 5% hydrochloric acid was added to the solution until the solution became acidic. The mixture was extracted with methylene chloride. The methylene chloride solution was washed with brine and dried over $MgSO_4$. The crude product was purified with flash column chromatography (silica; methylene chloride and methanol, 10:1) to afford the title compound: 30 mg, 17% yield, m.p., 169.6-170.3° C. $^1$H NMR (250 MHZ, $D_2O$—$CDCl_3$), δ1.25 (3H, t, J=7.0 Hz), 1.72 (1H, d, J=15 Hz), 1.90-2.15 (1H, m), 2.19 (3H, s), 2.36 (1H, t, J=12.5 Hz), 2.5-2.65 (1H, m), 2.7-3.0 (3H, m), 3.2-3.4 (4H, m), 3.4-3.6 (1H, m), 4.13 (1H, d, J=10.5 Hz), 6.71 (1H, s), 7.11 (2H, d, J=8.0 Hz), 7.43 (1H, s), 7.89 (2H, d, J=8.0 Hz). MS: 413 (M). Anal. ($C_{22}H_{25}O_2BrClN \cdot 1.8H_2O$): Calculated C, 54.68; H, 5.22; N, 2.90. Found C, 54.77; H, 5.52; N, 2.57. HRMS Calcd for $C_{22}H_{24}NO_2Br$ (corresponding to the free base): m/z 413.0990. Found: m/z 413.0994.

Example 6

Synthesis of (4aRS,5SR,9bRS)-2-Ethyl-8-Chloro-7-Methyl-2,3,4,4a,5,9b-Hexahydro-5-(4-carboxyphenyl)-1H-Indeno[1,2-c]pyridine Hydrochloride (20)

(4aRS,5SR,9bRS)-2-Ethyl-8-iodo-7-methyl-2,3,4,4a,5, 9b-hexahydro-5-(4-carboxylphenyl)-1H-indeno[1,2-c]pyridine hydrochloride (250 mg, 0.5 mmol) was dissolved in 25 mL THF and 0.5 mL HMPA. To this solution was added 60 mg sodium hydride (60% in mineral oil). The mixture was refluxed for 1 h and then cooled to −78° C. Tert-Butyllithium solution (0.91 mL, 1.1 M in pentane, 1.04 mmol) was added slowly. After the addition the mixture was stirred at −78° C. for 20 min. A solution of hexachloroethane (2.46 g, 10.4 mmol) in 2 mL THF was added. The mixture was stirred at −78° C. for another 30 min. and then warmed to room temperature. 5% Hydrochloric acid was added to the solution until the solution became acidic. The mixture was extracted with methylene chloride. The methylene chloride solution was washed with brine and dried over $MgSO_4$. The crude product was purified with flash column chromatography (methylene chloride and methanol, 10:1) to afford the title compound, 60 mg, 30% yield. $^1$H NMR (250 MHZ, $D_2O$-$CDCl_3$) δ1.35 (3H, t, J=7.25 Hz), 1.75-1.95 (1H, m), 2.30 (3H, s), 2.45-2.75 (2H, m), 2.80-3.15 (2H, m), 3.20-3.50 (4H, m), 3.50-3.70 (1H, m), 4.25 (1H, d, J=10 Hz), 6.80 (1H, s), 7.25 (2H, d, J=7.5 Hz), 7.32 (1H, s), 8.0 (2H, d, J=7.5 Hz). MS: 370 (M). Anal. ($C_{22}H_{25}O_2Cl_2N$): Calculated C, 65.50; H, 6.20; N, 3.45. Found C, 65.65; H, 6.73; N, 3.59. HRMS Calcd for $C_{22}H_{24}NO_2Cl$ (corresponding to the free base): m/z 369.1495. Found: m/z 369.1494.

Example 7

Synthesis of (4aRS,9bRS)-2-Ethyl-1,2,3,4,4a,9b-hexahydro-1H-indeno[1,2-c]pyridin-5-one (7)

Crude methyl 1-ethyl-3-(4-methylphenyl)-4-pyridinecarboxylate (prepared as described in U.S. Pat. No. 5,319,084 for the analogous ethyl ester) from 165 g of methyl 1-ethyl-1,2,5,6-tetrahydropyridinecarboxylate was dissolved in 1 L of aqueous 18% HCl and extracted with ether (300 ml) to remove bitolyl remaining as a byproduct from its synthesis. The aqueous solution was then refluxed for 48 hr and then concentrated under reduced pressure with added acetonitrile (azeotrope) to give crude 1-ethyl-1,2,5,6-tetrahydropyridinecarboxylic acid hydrochloride (283 g), which was dried thoroughly at 100° C. under high vacuum. As this material is very hygroscopic, it was stored under nitrogen. Thionyl chloride (150 mL) was added cautiously to neat 7 (45 g, 159 mmol) at 5° C. After the addition, the ice bath was removed; and the resulting homogeneous solution was stirred at room temperature for 4 h. Excess $SOCl_2$ was removed in vacuo to give a dark, thick, pasty mass. To this material was added 1,2-dichloroethane (250 mL) and 30 mL of solvent was removed in vacuo in order to remove any residual $SOCl_2$. To the turbid mixture was added $AlCl_3$ (53 g, 397 mmol) in portions over a 45 min period. The temperature was controlled by means of a water bath at ca. 25° C. After the addition, the dark, red-brown, solution was stirred at 35-40° C. for an hour and then poured into a beaker containing ca. 400 g of crushed ice and 50 mL of conc. HCl. The aqueous layer was basified to pH of ca. 12 with 30% NaOH (ca. 350 mL) with cooling in an ice water bath. The resulting mixture was extracted with cooling in an ice water bath. The resulting mixture was extracted with ether (3×400 mL), and the combined ether layers were washed successively with water and brine, dried ($MgSO_4$), filtered, and concentrated under reduced pressure to give an orange-red oil. This oil was distilled using a Kugelrohr apparatus (125-135° C. at 0.5 mm Hg) to give 21.6 g (59%) of ketone 7 as a bright yellow solid, with NMR properties identical with authentic material.

Example 8

Synthesis of Enantiomers of (4aRS,5SR,9bRS)-2-Ethyl-7-methyl-5-(4-carbomethoxyphenyl)-2,3,4,4a,5,9b-hexahydroindeno[1,2-c]pyridine and (4aRS,5SR,9bRS)-2-Ethyl-7-methyl-5-(4-carboxyphenyl)-2,3,4,4a,5,9b-hexahydroindeno[1,2-c]pyridine Enantiomers are described as (d) or (l) based on optical rotation at the sodium D line in the solvent given. Compounds having the same sign of rotation do not necessarily have the same absolute configuration.

1-Ethyl-4-carboxy-1,2,5,6-tetrahydropyridine Hydrochloride. Methyl 1-ethyl-1,2,5,6-tetrahydropyridinecarboxylate (11) was refluxed in 250 mL of 1.5 M HCl for 4 h. The mixture was concentrated to dryness using applied heat and a stream of nitrogen to give a highly crystalline solid. The solid was recrystallized from MeOH and gave 19.6 g of the HCl salt of 12; m.p.=265° C. (dec.). Anal. Calcd. for $C_8H_{14}ClNO_2$: C, 50.14; H, 7.36; N, 7.31. Found: C, 50.23; H, 7.36; N, 7.28.

(l)-Enoyl Sultam ((l)-13) derived from 1S(−)-(2,10)camphorsultam. To the hydrochloride of 12 (1.3 g, 6.79 mmol) was added thionyl chloride (15 mL), and the resulting mixture was heated to reflux for 2 h. Excess $SOCl_2$ was removed in vacuo, and the residue was triturated with 10 mL of dry toluene and concentrated in vacuo. The trituration process was repeated two more times to give a yellow, powdery solid. In a separate vessel, n-butyllithium (15 mmol, 6.0 mL of a 2.5 M solution in hexane) was added dropwise to a solution of 1S-(−)-2,10-camphorsultam (3.16 g, 14.7 mmol) in THF (30 mL) at 5° C. After the addition, the clear, colorless solution was brought to room temperature and stirred for an additional 45 min. The solution of sultam anion was then cannulated into the flask containing the amino acid chloride hydrochloride at 5° C. After the addition, the orange mixture was allowed to come to room temperature and stirred for 18 h. The reaction was quenched by the addition of saturated $NH_4Cl$ (ca. 1 mL) and concentrated in vacuo to a brown, tarry residue. The residue was partitioned between ether and water, and the ether layer was washed once more with water. The ether layer was then washed with dilute aqueous HCl (ca. 5%) and separated. The free sultam (ether layer) was obtained (1.2 g) upon recrystallization from absolute EtOH. The product [(l)-1,3] was obtained by basifying the acidic aqueous layer with conc. $NH_4OH$ to pH 12, extraction with ether and recrystallization from n-hexane of the residue from evaporation of the ether layer. This gave 1.9 g of (l)-13 as white, thick needles; m.p.=120° C., $[\alpha]_D^{21}=-74.80$ (c=1.0, $CHCl_3$), $^1H$ NMR identical with its antipode (see below). Anal. Calcd. for $C_8H_{28}N_2O_3S$: C, 61.33; H, 8.01; N, 7.95. Found: C, 61.35; H, 8.06; N, 7.89.

(d)-Enoyl Sultam enantiomer of 13 derived from 1R(+)-(2,10)-camphorsultam. This was prepared from the hydrochloride of amino acid 12 (6.5 g, 34.1 mmol) and 1R-(+)-2,10-camphorsultam (15.4 g, 71.4 mmol) in a procedure similar to that described for the antipode (see above) in 86% yield. m.p.=118.5° C.-119.6° C. (recrystallized from hexane as thick, straw-colored leaflets); $[\alpha]_D^{21}=+74.1°$ (c=1.0, $CHCl_3$); $^1H$ NMR (250 MHZ, $CDCl_3$): δ1.00 (3H, s), 1.12 (3H, t, J=7.1 Hz), 1.22 (3H, s), 1.3-1.5 (2H, m), 1.8-2.1 (5H, m), 2.2-2.4 (1H, m), 2.55 (2H, q, J=7.1 Hz), 2.6-2.7 (3H, m), 3.1-3.3 (2H, m), 3.38 (1H, d, J=13.6 Hz), 3.50 (1H, d, J=13.6 Hz), 4.0-4.1 (1 h, m), 6.5-6.6 (1H, m); Anal. Calcd. for $C_8H_{28}N_2O_3S$: C, 61.33; H, 8.01; N, 7.95. Found: C, 61.48; H, 8.02; N, 7.98. The crystalline form of this material varied depending on how fast it precipitated out of hexane and the concentration during the purification step.

1,4-Adduct(l)-14 derived from (l)-13. To a solution of enoyl sultam (l)-13 (5.6 g, 16.0 mmol) in toluene (200 mL) at −78° C. was added p-tolylmagnesium bromide (33.6 mmol, 33.6 mL of a 1.0M solution in ether) over 10 min. After being stirred an additional 30 min at −78° C., the reaction mixture was placed in a freezer (−10° C.). overnight and then warmed to +5° C. for two additional hours. The mixture was quenched by adding it to saturated $NH_4Cl$ (200 mL). After extraction of the aqueous layer with ether (400 mL), the ether layer was extracted with 3% HCl (3×200 mL). The acidic layers were combined, made basic with conc. $NH_4OH$ (pH=12), extracted with ether (3×200 mL), and the ether layers were washed with brine, dried ($MgSO_4$), filtered, and concentrated under reduced pressure to give an orange solid (7.12 g). This solid was recrystallized from ether-hexane (ca. 40 mL of an approximately 1:2 mixture, respectively). Yield=3.64 g. A second crop gave another 1.24 g. Total=4.68 g (66%). m.p.=150.5-151.7° C. (ether-hexane; dense, thick, straw-colored prisms); $[\alpha]_D^{21}=26.2°$ (c=1.14, $CHCl_3$); $^1H$ NMR (500 MHZ, $CDCl_3$); δ0.44 (3H, s), 0.82 (3H, s), 1.13 (3H, t, J=7.16 Hz), 1.20-1.30 (2H, m), 1.40-1.55 (1H, m), 1.62-1.65 (1H, m), 1.70-1.85 (3H, m), 1.95-2.05 (1H, m), 2.05-2.10 (1H, m), 2.27 (3H, s), 2.55 (2H, q, J=7.16 Hz), 2.55-2.62 (1H, m), 2.68-2.72 (1H, m), 2.82 (1H, dd, J=10.64, 3.47 Hz), 3.12 (1H, t, J=10.8 Hz), 3.24-3.28 (1H, m), 3.30 (1H, d, J=14.0 Hz), 3.32 (1H, d, J=14.0 Hz), 3.55-3.60 (1H, m), 3.67-3.71 (1H, m), 7.02 (2H, d, J=7.96 Hz), 7.15 (2H, d, J=7.96 Hz); Anal. Calcd. for $C_{25}H_{36}N_2O_3S$: C, 67.53; H, 8.16; N, 6.30. Found: C, 67.58; H, 8.15; N, 6.30.

Enantiomerically pure ketone (d)-7 derived from (1)-14. To a solution of the 1,4-adduct (1)-14 (6.86 g, 15.45 mmol) in THF (40 ml) was added to a freshly prepared solution of LiOH.multidot.$H_2O$ (6.43 g, 153 mmol) in water (40 mL). The resulting heterogeneous mixture was vigorously stirred at a gentle reflux for 26 h. The mixture was cooled to ca. +5° C., acidified to pH=0 with conc. HCl, and the bulk of the volatile components were removed by directing a moderately strong current of nitrogen gas over the surface of the mixture while it was immersed in a warm water bath (temp=50° C.). The remaining solid was thoroughly dried under high vacuum. The crude material obtained was cyclized to ketone (d)-7 in a manner similar to racemic material (see above) using thionyl chloride and then $AlCl_3$ in 1,2-dichloroethane. This yielded 1.12 g of free base ketone (d)-7 as an oil which solidified upon standing overnight. A portion of this material was purified after being recovered from the next step in order to get physical data. $[\alpha]_D^{20}$=+95.9° (free base, c=1.2, CHCl.sub.3); $[\alpha]_D^{20}$=+71.9° (HCl salt, c=1.1, $CHCl_3$).

Enantiomerically pure Olefin(d)-15 derived from ketone (d)-7. This material was obtained from ketone (d)-7 (1.12 g, 4.89 mmol) in a manner similar to the racemic procedure (see U.S. Pat. No. 5,319,084). The yield was 850 mg (47%). $[\alpha]_D^9$=+21.2° (c=1.24, $CHCl_3$).

The synthesis of (1)-2-Ethyl-7-Methyl-2,3,4,4a,5,9b-Hexahydro-5-(4-bromophenyl)-5-Hydroxy-1H-Indeno[1,2-c]pyridine. To a vigorously stirred solution of 4-bromoiodobenzene (13.8 g, 48.9 mmol) in 160 mL THF at −78° C. was added n-butyllithium solution (19.6 mL, 2.5 M in pentane, 49 mmol) very slowly. After the addition, the solution was stirred at −78° C. for 10 min. The solution became yellow and cloudy. A solution of (d)-2-Ethyl-7-methyl-1,2,3,4,4a,5,9b-hexahydroindeno[1,2-c]pyridin-5-one (8 g, 34.9 mM) in 40 mL THF was added. The mixture was then stirred at −78° C. for 2 h. The cooling bath was removed and the mixture was quenched with water. The organic phase was separated and the aqueous phase was extracted with methylene chloride. The organic phases were combined, washed with brine and dried over $MgSO_4$. Evaporation of the solvent afforded the crude product, which was recrystallized from methylene chloride to produce the title compound (10.8 g, 80%). m.p., 169.6-170.3° C. $^1$H NMR (250 MHZ, $CDCl_3$), δ1.00 (3H, t, J=7.3 Hz), 1.70-2.00 (2H, m), 2.15-2.30 (1H, m), 2.29 (3H, s), 2.38 (2H, q, J=7.3 Hz), 2.5-2.7 (2H, m), 2.70-2.85 (1H, m), 2.85-3.00 (1H, m), 3.30-3.50 (1H, m), 6.84 (1H, s), 7.17 (2H, q, J=7.5 Hz), 7.31 (2H, d, J=11 Hz), 7.43 (2H, d, J=11 Hz). MS: 386 (M), 230 (100%). $[\alpha]_D$=−11.5° (c=1.03, $CHCl_3$). Anal. ($C_{22}H_{24}OBrN$): Calculated C, 65.28; H, 6.26; N, 3.62. Found C, 65.11; H, 6.21; N, 3.64.

The Synthesis of the (I)-enantiomer of (4aSR,5RS,9bSR)-2-Ethyl-7-Methyl-2,3,4,4a,5,9b-Hexahydro-5-(4-bromophenyl)-1H-Indeno[1,2-c]pyridine (1). A solution of (1)-10-2-ethyl-7-methyl-2,3,4,4a,5,9b-hexahydro-5-(4-bromophenyl)-5-hydroxy-1H-indeno[1,2-c]pyridine (4, 5 g, 13 mmol) and 100 mL triethylsilane in 300 mL anhydrous methylene chloride was cooled to −78° C. Trifluoroborane gas was bubbled to the solution for 10 min. The colorless solution turned to orange. The mixture was warmed to room temperature and 10 g potassium carbonate was added, followed by water. The organic phase was separated and the aqueous phase was extracted with methylene chloride. The organic phases were combined, washed with brine and dried over $MgSO_4$. The solvent was evaporated to give the crude product.

The crude product was dissolved in 40 mL n-butanol. Potassium hydroxide (9 g) was added. The mixture was heated to reflux with stirring. After being refluxed for 20 h, the mixture was cooled to room temperature and poured into ice. The mixture was extracted with methylene chloride. The methylene chloride solution was washed with brine and dried over $MgSO_4$. The solvent was evaporated and the crude product was partitioned between diethyl ether and 18% hydrochloric acid solution. Layers were separated and the aqueous solution was washed one more time with diethyl ether. The aqueous solution was cooled to 0° C. and basified with 50% sodium hydroxide solution to pH>14. The mixture was extracted with methylene chloride three times. The organic solution was washed with brine and dried over $MgSO_4$. Evaporation of the solvent afforded the crude product, which was purified with flash column chromatography (silica gel, $CH_2Cl_2$ and MeOH, 100:3) to give the title compound (1)-10, 3.2 g, 67% yield (over two steps). The hydrochloride salt was made in the usual manner. m.p. 240° C. (decompose). $^1$H NMR (250 MHZ, $CDCl_3$), δ1.12 (3H, t, J=7.25), 1.6-1.8 (1H, m), 1.80-2.05 (2H, m), 2.15-2.40 (2H, m), 2.26 (3H, s), 2.70-2.85 (1H, m), 2.90-3.10 (1H, m), 3.30-3.45 (1H, m), 4.12 (1H, d, J=10.25 Hz), 6.72 (1H, s), 7.00-7.30 (4H, m), 7.44 (2H, d, J=9.0 Hz). MS: 370 (M). $[\alpha]_D$=−7.8° (c=0.83, MeOH). Anal. ($C_{21}H_{24}BrN.HCl$): Calculated C, 62.00; H, 6.19; N, 3.44. Found C, 61.96; H, 6.23; N, 3.35.

The Synthesis of (1)-Enantiomer of (4aRS,5SR,9bRS)-2-Ethyl-2,3,4,4a,5,9b-hexahydro-7-methyl-5-(4-carboxyphenyl)-1H-indeno[1,2-c]pyridine Hydrochloride[(1)-2]. A solution of 100 mg (0.27 mmol) of (1)-10 compound in 5 mL THF was cooled to −78° C. To this solution was added 0.54 mL n-butyllithium solution (2.5 M in pentane, 1.35 mmol). The solution was stirred at −78° C. for 30 min. Carbon dioxide gas was bubbled into the solution for 10 min through a needle. The mixture was stirred at −78° C. for 10 more minutes and warmed to room temperature. THF was evaporated and the residue was acidified with 18% hydrochloric acid. The mixture was extracted with methylene chloride. The methylene chloride solution was washed with brine and dried over $MgSO_4$. The drying reagent was filtered and the solution was concentrated to give the crude product. Column chromatography (silica gel, $CH_2Cl_2$ and MeOH, 10:1 to 1:1) of the crude product afforded 72 mg (71% yield) (−)-2. $[\alpha]_D$=−15.5° (c=1.24, MeOH).

Synthesis of the (d)-Enantiomer of (4aRS,5SR,9bRS)-2-Ethyl-2,3,4,4a,5,9b-hexahydro-7-methyl-5-(4-carbomethoxyphenyl)-1H-indeno[1,2-c]pyridine Hydrochloride [(d)-3]. A solution of (1)-2 (20 mg) in 1 mL methanol was cooled to −10° C. (ice-acetone). Excess thionyl chloride was added. After the addition, the mixture was warmed to room temperature and stirred overnight. Excess thionyl chloride and the solvent were blown away with nitrogen and the residue was dried under vacuum. The crude product was analyzed with HPLC (Sumichiral, QA-4900, 4 mm×25 cm; Solvents: 53.8% 1,2-dichloroethane, 44% hexane, 2.2% ethanol, and 0.1% TFA; Flow Rate: 0.8 mL/min; λ=254 nm), which showed >97% ee of (d)-3.

Synthesis of the (d)-Enantiomer of (4aRS,5SR,9bRS)-2-Ethyl-2,3,4,4a,5,9b-hexahydro-7-methyl-5-(4-carboxyphenyl)-1H-indeno[1,2-c]pyridine Hydrochloride[(d)-2] and of the (1)-Enantiomer of (4aRS,5SR,9bRS)-2-Ethyl-2,3,4,4a,5, 9b-hexahydro-7-methyl-5-(4-carbomethoxy phenyl)-1H-indeno[1,2-c]pyridine Hydrochloride[(1)-3]. These two compounds may be synthesized by starting with enoylsultam (d)-13 described above and carrying out the subsequent steps above used for the synthesis of the ir enantiomers. Their properties have been previously described. See Cook et al., J. Med. Chem., 38:753-763 (1995).

Obviously, numerous modifications and variations of the present invention are possible in light of the above teachings. It is therefore to be understood that, within the scope of the appended claims, the invention may be practiced otherwise than as specifically described herein

The invention claimed is:

1. A method for killing motile spermatozoa, comprising:
contacting a spermatozoa containing composition with a spermicidal composition comprising a compound of formula I(a):

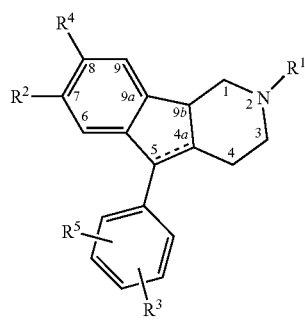

wherein $R^1$ is hydrogen or straight-chain or branched $C_{1-6}$ alkyl or $C_3$-$C_8$ cycloalkyl;
$R^2$ is hydrogen, straight-chain or branched $C_{1-6}$ alkyl;
$R^3$ and $R^5$ are each, independently, hydrogen, $SO_3H$, straight-chain or branched $C_{1-6}$ alkyl, $CH_2OH$, $CH_2OMe$, straight chain or branched $C_{1-6}$ alkoxy, carboxyl (COOH), carboxylic acid ester (COOR where R is $C_{1-10}$ alkyl, $C_{6-10}$ aryl, $C_{7-10}$ aralkyl), hydroxymethyl ester ($CH_2$ OC(O)—R where R is as defined above), $CONH_2$, CONHR, $CONR_2$, $CH_2OCONHR$, CN, CH=$NHNHCONH_2$, and halogen; and
$R^4$ is hydrogen, halogen, $R_3Si$ or COR,
or a pharmaceutically acceptable salt thereof.

2. The method of claim 1, wherein the compound is a compound of formula I(b):

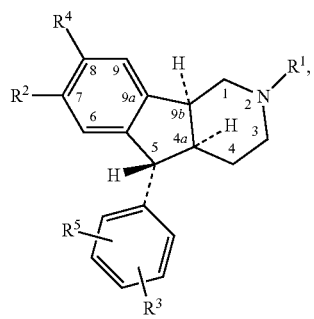

or a pharmaceutically acceptable salt thereof.

3. The method of claim 1, wherein $R^1$ is a member selected from the group consisting of hydrogen, methyl, ethyl, n-propyl, iso-propyl, n-butyl, iso-butyl, n-pentyl, iso-pentyl, n-hexyl, iso-hexyl, cyclopropyl, cyclopentyl, and cyclohexyl;

$R^2$ is a member selected from the group consisting of hydrogen, methyl, ethyl, n-propyl, iso-propyl, n-butyl, iso-butyl, n-pentyl, iso-pentyl, n-hexyl and iso-hexyl;
$R^3$ is at the 4 position and is a member selected from the group consisting of hydrogen, $SO_3H$, straight-chain or branched $C_{1-6}$ alkyl, $CH_2OH$, $CH_2OMe$, straight chain or branched $C_{1-6}$ alkoxy, carboxyl (COOH), hydroxymethyl ($CH_2$ OH), formyl (CHO), carboxyl (COOH), carboxylic acid ester (COOR where R is $C_{1-10}$ alkyl, $C_{6-10}$ aryl, or $C_{7-10}$ aralkyl), hydroxymethyl ester ($CH_2$ OC(O)—R where R is as defined above), $CONH_2$, CONHR, $CONR_2$, $CH_2OCONHR$, CN, CH=$NHNHCONH_2$, and halogen;
$R^5$ is hydrogen; and
$R^4$ is a member selected from the group consisting of hydrogen and halogen,
or a pharmaceutically acceptable salt thereof.

4. The method of claim 3, wherein $R^1$ is methyl, ethyl, n-propyl or iso-propyl;
$R^2$ is methyl, ethyl, n-propyl or iso-propyl;
$R^3$ is 4-COOH or 4-COOR, where R is as defined above;
$R^5$ is hydrogen; and
$R^4$ is halogen,
or a pharmaceutically acceptable salt thereof.

5. A contraceptive method, comprising:
orally administering to a subject, a composition comprising an effective antispermatogenic amount of a first compound of formula I(a):

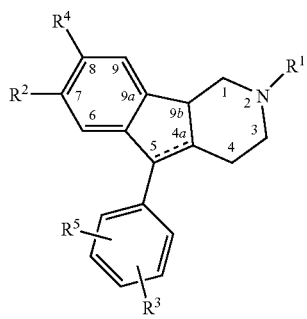

wherein $R^1$ is hydrogen or straight-chain or branched $C_{1-6}$ alkyl or $C_3$-$C_8$ cycloalkyl;
$R^2$ is hydrogen, straight-chain or branched $C_{1-6}$ alkyl;
$R^3$ and $R^5$ are each, independently, hydrogen, $SO_3H$, straight-chain or branched $C_{1-6}$ alkyl, $CH_2OH$, $CH_2OMe$, straight chain or branched $C_{1-6}$ alkoxy, carboxyl (COOH), a non-ester group which can be converted under mammalian physiological conditions to a carboxyl group, carboxylic acid ester (COOR where R is $C_{1-10}$ alkyl, $C_{6-10}$ aryl, $C_{7-10}$ aralkyl), hydroxymethyl ester ($CH_2$ OC(O)—R where R is as defined above), $CONH_2$, CONHR, $CONR_2$, $CH_2OCONHR$, CN, CH=$NHNHCONH_2$, and halogen; and
$R^4$ is hydrogen, halogen, $R_3Si$ or COR, or a pharmaceutically acceptable salt thereof;
in a pharmacologically acceptable carrier; and
concurrent use by said subject of a spermicidally treated contraceptive barrier device comprising:
an effective spermicidal amount of a second compound of formula I(a):

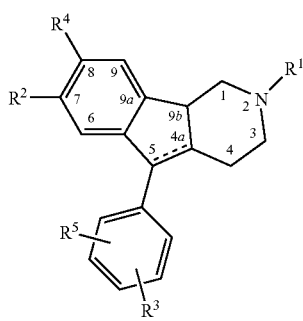

wherein $R^1$ is hydrogen or straight-chain or branched $C_{1-6}$ alkyl or $C_3$-$C_8$ cycloalkyl;

$R^2$ is hydrogen, straight-chain or branched $C_{1-6}$ alkyl;

$R^3$ and $R^5$ are each, independently, hydrogen, $SO_3H$, straight-chain or branched $C_{1-6}$ alkyl, $CH_2OH$, $CH_2OMe$, straight chain or branched $C_{1-6}$ alkoxy, carboxyl (COOH), a non-ester group which can be converted under mammalian physiological conditions to a carboxyl group, carboxylic acid ester (COOR where R is $C_{1-10}$ alkyl, $C_{6-10}$ aryl, $C_{7-10}$ aralkyl), hydroxymethyl ester ($CH_2$ OC(O)—R where R is as defined above), $CONH_2$, CONHR, $CONR_2$, $CH_2OCONHR$, CN, $CH=NHNHCONH_2$, and halogen; and $R^4$ is hydrogen, halogen, $R_3Si$ or COR, or a pharmaceutically acceptable salt thereof;

and a carrier;

wherein said first compound of formula I(a) and said second compound of formula I(a) may be the same or different.

6. The method of claim 5, wherein the first compound is a first compound of formula I(b):

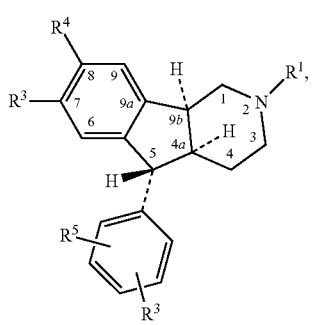

or a pharmaceutically acceptable salt thereof.

7. The method of claim 5, wherein in said first compound of formula I(a), $R^1$ is a member selected from the group consisting of hydrogen, methyl, ethyl, n-propyl, iso-propyl, n-butyl, iso-butyl, n-pentyl, iso-pentyl, n-hexyl, iso-hexyl, cyclopropyl, cyclopentyl, and cyclohexyl;

$R^2$ is a member selected from the group consisting of hydrogen, methyl, ethyl, n-propyl, iso-propyl, n-butyl, iso-butyl, n-pentyl, iso-pentyl, n-hexyl and iso-hexyl;

$R^3$ is at the 4 position and is a member selected from the group consisting of hydrogen, hydroxymethyl ($CH_2$ OH), formyl (CHO), carboxyl (COOH), carboxylic acid ester (COOR where R is $C_{1-10}$ alkyl, $C_{6-10}$ aryl, or $C_{7-10}$ aralkyl), hydroxymethyl ester ($CH_2$ OC(O)—R where R is as defined above), $CONH_2$, CONHR, $CONR_2$, $CH_2OCONHR$, CN, $CH=NHNHCONH_2$, and halogen;

$R^5$ is hydrogen; and $R^4$ is a member selected from the group consisting of hydrogen and halogen, or a pharmaceutically acceptable salt thereof.

8. The method of claim 7, wherein in said first compound of formula I(a), $R^1$ is methyl, ethyl, n-propyl or iso-propyl;

$R^2$ is methyl, ethyl, n-propyl or iso-propyl;

$R^3$ is 4-COOH or 4-COOR, where R is as defined above;

$R^5$ is hydrogen; and $R^4$ is halogen, or a pharmaceutically acceptable salt thereof.

9. The method of claim 5, wherein said contraceptive barrier device is a member selected from the group consisting of diaphragms, contraceptive sponges and condoms.

10. The method of claim 5, wherein the second compound is a second compound of formula I(b):

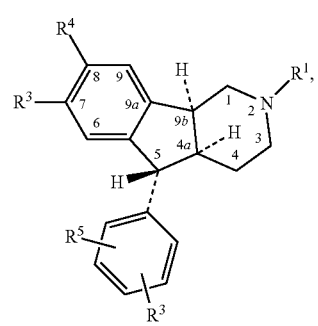

or a pharmaceutically acceptable salt thereof.

11. The method of claim 5, wherein in said second compound of formula I(a), $R^1$ is a member selected from the group consisting of hydrogen, methyl, ethyl, n-propyl, iso-propyl, n-butyl, iso-butyl, n-pentyl, iso-pentyl, n-hexyl, iso-hexyl, cyclopropyl, cyclopentyl, and cyclohexyl;

$R^2$ is a member selected from the group consisting of hydrogen, methyl, ethyl, n-propyl, iso-propyl, n-butyl, iso-butyl, n-pentyl, iso-pentyl, n-hexyl and iso-hexyl;

$R^3$ is at the 4 position and is a member selected from the group consisting of hydrogen, hydroxymethyl ($CH_2$ OH), formyl (CHO), carboxyl (COOH), carboxylic acid ester (COOR where R is $C_{1-10}$ alkyl, $C_{6-10}$ aryl, or $C_{7-10}$ aralkyl), hydroxymethyl ester ($CH_2$ OC(O)—R where R is as defined above), $CONH_2$, CONHR, $CONR_2$, $CH_2OCONHR$, CN, $CH=NHNHCONH_2$, and halogen;

$R^5$ is hydrogen; and $R^4$ is a member selected from the group consisting of hydrogen and halogen, or a pharmaceutically acceptable salt thereof.

12. The method of claim 11, wherein in said second compound of formula I(a), $R^1$ is methyl, ethyl, n-propyl or iso-propyl;

$R^2$ is methyl, ethyl, n-propyl or iso-propyl;

$R^3$ is 4-COOH or 4-COOR, where R is as defined above;

$R^5$ is hydrogen; and $R^4$ is halogen, or a pharmaceutically acceptable salt thereof.

13. The method of claim 5, wherein said first compound of formula I(a) and said second compound of formula I(a) are the same.

14. The method of claim 5, wherein said first compound of formula I(a) and said second compound of formula I(a) are different.

15. The method of claim 6, wherein said first compound of formula I(a) and said second compound of formula I(a) are the same.

16. The method of claim 6, wherein said first compound of formula I(a) and said second compound of formula I(a) are different.

17. The method of claim 7, wherein said first compound of formula I(a) and said second compound of formula I(a) are the same.

18. The method of claim 7, wherein said first compound of formula I(a) and said second compound of formula I(a) are different.

19. The method of claim 8, wherein said first compound of formula I(a) and said second compound of formula I(a) are the same.

20. The method of claim 8, wherein said first compound of formula I(a) and said second compound of formula I(a) are different.

21. The method of claim 9, wherein said first compound of formula I(a) and said second compound of formula I(a) are the same.

22. The method of claim 9, wherein said first compound of formula I(a) and said second compound of formula I(a) are different.

23. The method of claim 10, wherein said first compound of formula I(a) and said second compound of formula I(a) are the same.

24. The method of claim 10, wherein said first compound of formula I(a) and said second compound of formula I(a) are different.

25. The method of claim 11, wherein said first compound of formula I(a) and said second compound of formula I(a) are the same.

26. The method of claim 11, wherein said first compound of formula I(a) and said second compound of formula I(a) are different.

27. The method of claim 12, wherein said first compound of formula I(a) and said second compound of formula I(a) are the same.

28. The method of claim 12, wherein said first compound of formula I(a) and said second compound of formula I(a) are different.

\* \* \* \* \*